United States Patent [19]

Chiang

[11] Patent Number: 5,650,286
[45] Date of Patent: Jul. 22, 1997

[54] GENOMIC DNA OF HUMAN CHOLESTEROL 7α-HYDROXYLASE AND METHODS FOR USING IT

[75] Inventor: John Young Ling Chiang, Stow, Ohio

[73] Assignee: Northeastern Ohio University, Rootstown, Ohio

[21] Appl. No.: 483,852

[22] Filed: Jun. 7, 1995

Related U.S. Application Data

[63] Continuation of Ser. No. 361,458, Dec. 21, 1994, which is a continuation of Ser. No. 135,488, Oct. 13, 1993, abandoned.

[51] Int. Cl.$^6$ .................................................. C12Q 1/26
[52] U.S. Cl. .................................................. 435/7.6; 435/189
[58] Field of Search ............................... 435/7.6, 189

[56] References Cited

PUBLICATIONS

Karam, W. G. et al., "Polymorphisms of Human Cholesterol 7α-Hydroxylase", *Biochem. and Biophys. Res. Comm.* 185(2): 588–595 (1992).

Breslow, J. L. et al., "Transgenic Mouse Models of Lipoprotein Metabolism and Atherosclerosis", *Proc. Natl. Acad. Sci. USA* 90: 8314–8318 (1993).

Cohen, J. C. et al., "Cloning of the Human Cholesterol 7α-Hydroxylase Gene (CYP7) and Localization to Chromosome 8q11–q12", *Genomics* 14: 153–161 (1992).

Nishimoto, M. et al., "Structure of the Gene Encoding Human Liver Cholesterol 7α-Hydroxylase", *Biochimica. et Biophysica. Acta.* 1172: 147–150 (1992).

Thompson, J. F. et al., "Cholesterol 7α-Hydroxylase Promoter Separated from Cyclophilin Pseudogene By Alu Sequence", *Biochimica et Biophysica Acta* 1168: 239–242 (1993).

Li, Y. C. et al., "The Expression of a Catalytically Active Cholesterol 7α-Hydroxylase Cytochrome P450 in *Escherichia coli*", *The Journal of Biological Chemistry* 266(29): 19186–19191 (1991).

Molowa, D. T. et al., "Transcriptional Regulation of the Human Cholesterol 7α-Hydroxylase Gene", *Biochemistry* 31: 2539–2544 (1992).

Nishimoto, M. et al., "Structural Analysis of the Gene Encoding Rat Cholesterol α-Hydroxylase, The Key Enzyme for Bile . . . ", *The Journal of Biological Chemistry* 266(10): 6467–6471 (1991).

Jelinek, D. F. et al., "Structure of the Rat Gene Encoding Cholesterol 7α-Hydroxylase", *Biochemistry* 29(34): 7781–7785 (1990).

Chiang, J. Y. L. et al., "Cloning and 5'-Flanking Sequence of a Rat Cholesterol 7α-Hydroxylase", *Biochimica et Biophysica Acta* 1132: 337–339 (1992).

Lusis, Aldons J., "The Mouse Model for Atherosclerosis", *TCM* 3(4): 135–143 (1993).

Dueland, Svein et al., "Effect of Dietary Cholesterol and Taurocholate on Cholesterol 7α-hydroxylase and Hepatic LDL Receptors in Inbred Mice", *Journal of Lipid Research* 34: 923–931 (1993).

Dueland, Svein et al., "Expression of 7α-Hydroxylase in Non–hepatic Cell Results in Liver Phenotypic Resistance of the Low Density Lipoprotein Receiptor to Cholesterol Repression", *J. Bio. Chem.* 267(32): 22695–22698 (1992).

Ness et al., "Effect of Thyroid Hormone on Hepatic Cholesterol 7α-Hydroxylase, LDL Receptor, HMG–CoA Reductase, Farnesyl Pyrophosphate Synthetase and Apolipoproteein A–I mRNA Levels in Hypophghysectomized Rats", *Biochem. Res. Comm.* 172(3): 1150–1156 (1990).

G. Ciliberto et al., *EMBO J* 6: 4017–4022 (1987).

J.W. Gordon et al., *Science* 214: 1244–1246 (1981).

R.L. Brinster et al., *Proc. Natl. Acad. Sci. USA* 85: 836–840 (1988).

Abstract of M. Noshiro et al., "Molecular cloning and sequence analysis of cDNA encoding human cholesterol 7α-hydroxylase", *FEBS Lett.* 268(1): 137–140 (1990).

Sambrook et al., *Molecular Cloning: A Laboratory Manual*, 2nd Edition, Cold Spring Harbor Laboratory Press, 16.1–16.72 and 17.1–17.41 (1989).

M. Ramirez et al., "Cholesterol and Bile Acids Regulate Cholesterol 7α-Hydroxylase Expression at the Transcriptional Level in Culture and in Transgenic Mice", *Mol. Cell. Biol.* 14(4): 2809–2821 (1994).

*Primary Examiner*—Charles L. Patterson, Jr.
*Attorney, Agent, or Firm*—Foley & Lardner

[57] ABSTRACT

Genomic DNA of cholesterol 7α-hydroxylase and a minigene are disclosed. The minigene is used for making a transgenic animal that produces functionally active cholesterol 7α-hydroxylase and functions as a disease model. A cholesterol 7α-hydroxylase promoter region and reporter gene construct is provided, as well as a transgenic animal that expresses the promoter/reporter gene.

3 Claims, 18 Drawing Sheets

FIG. 1A Gene

```
  1 MMTTSLIWGIAIAACCLWLILGIRRRQTG
 31 EPPLENGLIPYLGCALQFGANPLEFLRANQ
 61 RKHGHVFTCKLMGKYVHFITNPLSYHKVLC
 91 HGKYFDWKKFHFATSAKAFGHRSIDPMDGN
121 TTENINDTFIKTLQGHALNSLTESMMENLQ
151 RIMRPPVSSNSKTAAWVTEGMYSFCYRVMF
181 EAGYLTIFGRDLTRRDTQKAHILNNLDNFK
211 QFDKVFPALVAGLPIHMFRTAHNAREKLAE
241 SLRHENLQKRESISELISLRMFLNDTLSTF
271 DDLEKARTHLVVLWASQANTIPATFWSLFQ
301 HIRNPEAMKAATEEVKRTLENAGQKVSLEG
331 NPICLSQAELNDLPVLDSHIKESLRLSSAS
361 LNIRTAKEDFTLHLEDGSYNIRKDDIIALY
391 PQLMHLDPRIYPDPLTFKYDRYLDENGKTK
421 TTFYCNGLKLKYYYMPFGSGATICPGRLFA
451 IHEIKQPLILMLSYFELELIEGQAKCPPLD
481 QSRAGLGILPPLNDIEPKYKFKHL*
```

FIG. 4A

```
  1  TTTTGGTTA TCTTTTCAGC CGTGCCCCAC TCTACTGGTA CCAGTTTACT GTATTAGTCG
 61  ATTTCATGC TGCTGATAAA GACATAGACA AAACTGGACA ATTTACAAAA GAAAGAGGTT
121  TATTGGACTT ACAATTCTAC ATCACTTGGG AGGCCTCACA ATCATGATGG AAGGAGAAAG
181  GCACATCTCA CATGGCAGCA GACAAGAAAA GAGCTTGTGC AGGGAAACTC CTCTTTTTAA
241  AACCATCAGA TCTCATGAAA TTTATTCATT ATCATGACAA TAGCACAGGA AAGAACTGCA
301  CCCATAATTC AGTCACCTCC TACCAGGTTC CTCCCACAAC ACGTGAGAAT TCAAGATGAG
361  ATTGGATGG GGACACAGCC AAACCATGGT ACACTACCAT GCCTGACTTC CTTTCCATTT
421  TTGTATATTT GCTTGTTCTT CATTGCCCG AGAAGTAACT CTAAAGGGCT GTATTATTTG
481  GATATTAGAT TGGCATTTTA TCTGACTGGG ATATCTTGCT GTGATTGTCC ATGTATAAGA
541  TCAGCTTTTC TATAAGCCAT ATTTTTAAAA AGATATATTA ATTTTTTAAA AATCCACCTG
601  TCTAAATAAA TGCACAAAGC CCCCAAAAGC CCTAGATTCT AAGAAAATC TATGTACTGC
661  CATACAATGA TTGATATTAA TATTTATGGT GATAAATTAC ACACAAAAAA TGTGTGATCT
721  CTGTTTAAAC AGGCAAAAAC AAAAAACACA TGAAATAAAT CTATGGCATC TATAGCCAAA
781  ACTGGAAACA ACCCACATAT CCATCAATAG GAAATCAGTT AATAAATTA TAGTACATTT
841  ATCCAATGGA AGATTAAGCA CATATTCAAT ATAATTATTT ATACACACAT ATAGATACAC
```

FIG. 4B

```
 901 ACATGTATAA ATATAGAGAA TACTGTGGGT GTATGTGTGT GTGTGTTTAT ATACATATAT
 961 ATACACACAC AGTACTGTTG CCTACCTTCT TTTGTCTTAA TTCTGTGAAC TCTCATTCAC
1021 TCTGCTTCAG TAGGATACCT CCTTCTTTTT GGTTCTTAGA CTCACCAAGT TGATCCTTGA
1081 CTCAAGACAT TGCATTTGCT GCTTCCTCTT CCTGGAATAT CCTTCCTTCT GATATTCACA
1141 TGAGTAGTCT CTTCTTGTCA TTCAGATCTC AAATGTCACA ATTTCAGAGA GCCCATCTCT
1201 GATCATCATA TCTAAAGTTG TCCTCATTCC CCCATAGCTT TCTATACCAT GTTTTATTTT
1261 TTTCATAACA TGTATTTTAT TACTCCTTTC TCCATTGGAA TAGAATCTCC ATTAGATTAG
1321 GAAATCTGCC TATCTTATTA ATGCCTGCAA CTGGAATACT TTTGAAGAGT TCTTGGCACG
1381 TAATAAATAC TCAACTAATA TTTTTGTGTA CACAGAAATA AAGTTTGGAA GAACAGATGC
1441 CAAATTGTTA CTAGTGGTTA CTTCTGAGTA AAGGAGTAGC ATGGTAGGTA AATTATTAAT
1501 AGATGTTCAC TTTCCACCAA GATATGTTTT AGTTAGTCTT AACTTACTTG AAATGAAATT
1561 TATTACTTTA ATAATTAGAA ACATTGATAA ACATTTTAGT CACAAGAATG ATAGATAAA
1621 TTTTGATGCT TCCAATAAGT TATATTTATC TAGAGGATGC ACTTATGTAG AATACTCTCT
1681 TGAGGATGTT AGGTGAGTAA CATGTTACTA TATGTAGTAA AATATCTATG ATTTTATAAA
```

FIG. 4C

```
1741 AGCACTGAAA CATGAAGCAG CAGAAATGTT TTTCCCAGTT CTCTTTCCTC TGAACTTGAT
1801 CACCGTCTCT CTGGCAAAGC ACCTAAATTA ATTCTTCTTT AAAAGTTAAC AAGACCAAAT
1861 TATAAGCTTG ATGAATAACT CATTCTTATC TTTCTTTAAA TGATTATAGT TTATGTATTT
1921 ATTAGCTATG CCCATCTTAA ACAGGTTTAT TTGTTCTTTT TACACATACC AAACTCTTAA
1981 TATTAGCTGT TGTCCCCAGG TCCGAATGTT AAGTCAACAT ATATTGAGA GACCTTCAAC
2041 TTATCAAGTA TTGCAGGTCT CTGATTGCTT TGGAACCACT TCTGATACCT GTGGACTTAG
2101 TTCAAGGCCA GTTACTACCA CTTTTTTTT TCTAATAGAA TGAACAAATG GCTAATTGTT
2161 TGCTTTGTCA ACCAAGCTCA AGTTAATGGA TCTGGATACT ATGTATATAA AAAGCCTAGC
2221 TTGAGTCTCT TTTCAGTGGC ATCCTTCCCT TTCTAATCAG AGATTTTCTT CCTCAGAGAT
2281 TTTGGCCTAG ATTTGCAAAA TGATGACCAC ATCTTTGATT TGGGGATTG CTATAGCAGC
2341 ATGCTGTTGT CTATGGCTTA TTCTTGGAAT TAGGAGAAGG TAAGTAATGT TTTATCTTTA
2401 AATTGCTCTT TGATTCATCC ATTTAATTTT TTTACCTTCA TTTTTATACA GTAAATTTGG
2461 TTTTCTATAC TTACACATAT TAGCATTATC TCCTTATGT TTTAAATGAA AAATTTGATT
2521 TGAATTTTA AGTAAATATC TTTTTTACTA TATCTCACAA GACATATGAC AGCTTCCTT
```

FIG. 4D

```
2581 TTAGTATTG GCATATACCG ATGGTAATAT ATAAATGTAT ATTGGTGTTA AACATAACTG
2641 ACAGAAATTG TATAAGGTCT CTATGTACAT TTATATGTGT ATCTAAAGAG GAAGCCCAGA
2701 TTAGTAAGGA TACAAGTAGC AAGTGGGAAT CTACAATGGA AAGGATTGCT TTCTCTCACA
2761 TGGCTTCAAT AGATACTCTT GCTTAAATAA ATGTTCTCTT TTAAGCTCAT TCTTGTGCAT
2821 CGCATAGACT CAGCCCTAAGC CTGAACAAGA GCATAGAGCC TGAGCTGATC ATTCTATTAC
2881 TGTTTTTAAA TAAATGTTAA TCAACTGTGG TGAATTGGGA AAGTTTGCTG AGTGTATGTG
2941 ACATCGATTT CATTTATTTA CAACTGTTC AAGAATGCAA GAAAAACAAA TACAGTCAGA
3001 TCCAGAACCA TAGTTTATTT AACTTCTAAT TGGCTCAAGG AGTAATTGTG GGGAGGCATA
3061 TAGATATTCT CTGCTATGTC AATCTCAAAA AGAGAAAATA ACCCTAACCA TCTTTCAGCT
3121 TTGTAGATTG CTATGTGTTT TCTGCCTTTG CAGTTTCTTT CAGGCCTGAT AGTTTTTACT
3181 TTTAATTAAA CTACTTATCT TCAAACTAAG AAAAGAAAGG TAATTACTTT ATACTGTATT
3241 ATTCTATCAA GAGGTACAGA AGTTTATGTT GGAAATAAG TTTACATGTT CTAATAAAAA
3301 CATTTTAAAG GAGCACTGAA TTACAATAGA TGATTCCGTC AGTGTTTATC TTACTCAATT
3361 TCATTTTATA ATAAGCTGAT TTCTCACATG AGATTCTTCT TCTCTGAAAC CATCCTTATA
3421 GAATATAATA TAGATATCTT TAAACTAGGA ATATTTTCAA AACCTCAGTT CTGAAATCCT
```

FIG. 4E

```
3481 CCCTTATTCA GTGATCTGTG TCTTTAAGGA AAATAATCAA AAGAAACATT TTGAGATATT
3541 TAGAAAAATG ATGCTTAGCA AAGTGATAAA CACTAGAATG TAGTTTTGTT TCCGCACTGA
3601 CAACAAGAAT CTTGTTGGTC TTGTAAATCC TTTTGCCTGT ATCACTGGGA AAAGTGATGA
3661 GCACATAGTA GACGGGTGCT TGTTGAATGT GTATATGGAC GGATGCATGA ATGGATGGAT
3721 TTAGTAATCC TTTCCACCAA CATATCATGT TACTAGGTTA ATATAACCTA TTACTGTAGT
3781 AAAAGAGCAG GGCCATCCA ACAAAAGAAA TATCTATAAA CTATAGGGTT TCAAAGTTTG
3841 AAGTCAGTGG GAAAATTTT AAAACCTGAT GTAAGTAAAA ACCCAAAACT GTAATCATCC
3901 ATGTCTATCA TACACTTGTG TCTGACAGGC AAACGGGTGA ACCACCTCTA GAGAATGGAT
3961 TAATTCCATA CCTGGCTGT GCTCTGCAAT TTGGTGCCAA TCCTCTTGAG TTCCTCAGAG
4021 CAAATCAAAG GAAACATGGT CATGTTTTTA CCTGCAAACT AATGGAAAAA TATGTCCATT
4081 TCATCACAAA TCCCTTGTCA TACCATAAGG TGTTGTGCCA CGGAAAATAT TTTGATTGGA
4141 AAAATTTCA CTTTGCTACT TCTGCGAAGG TAAGCAGTTT TACATTTATA TACCATTCTG
4201 TTTGTCTTCT ACCTTTTTAT GTGCTTGTCT ATTTAGAAAT TTGATGTAC TTAGATTTTA
4261 TGATAAAGGT GTTGAAGAGA GTTATCCTTA TGTGGAGATT CTTAGAAACA TAAATAAATT
4321 ATACGTAGCT TCTTAGTAAT AATCATTTAG AAAGTCAAAA TAGTATAGA TTTCCGTCAT
4381 TTGCTTTGCA CGAGCTAATG AGGGTGAAAT ACAGATTAAA TGCTCTACTG AGACAGGTGG
4441 CACTGTACGA ATAAGATAGA TTAAAATTCA TCACATCAGC AATGTCTATG CAGAGCGAAG
4501 TGACGGAAAC CTAACATTCA GCAGTTGTCT CACCACACTT GTGCCACACA GTGTTTCATT
```

FIG. 4F

```
4561 TTGATAAGGA ATTGGCAAGA TATTTAACA TCATTTAGAT GTAATAAAG AAGATCTGTT
4621 ACTGAGAAAA AAACCAATA AGCTTAAAGT ACTACTTACT TACTGCAAAT AAATATTAGC TTTGGTCTTT
4681 GTGACTAAGT AGCTTAAAGT TTGGTTAAAA TACATCTACA GCTGGACACA ATGGAACACA
4741 CCTGTAGTCC CTGCTATTTG AGAGGCTGAG GCAGGAGGAT CGCTTGAGTC CAGGAGTTTG
4801 AGGCTGCAGT GAGCTATCAT TGTGTCACTG CACTCCAGCC TGGGTGACAA TGTGAGACCC
4861 CATCTCTAAA AGAAAAAGAA AAAGAAATCT ACAAATAATA TAAAAGATAA CTAATGATTT
4921 TAAACATTA TCAATTAGTT TATGTGCAAT AGCTGTAAAT AAGTGCAGTA GCATAAGAAA
4981 TAAGACATAG ATGACTTGAG TGATCCAGGG GAGTGCCACT GAAGTTGGCT TTAAAGGAAA
5041 GGTACAGTTT GGTCATTTAT TTGTAAGTG CTATGAACTT GTACAAGGGA AAGCCAATTT
5101 CCCGTGTTTA CCAAGTAAGG AACTATGAAA GTATCTAATC CGTTTTTCAG TCATTTACTA
5161 TGACTAGTC AGGTTTAACT TCTTTTTCTG CATGTTTTAT TTGCTATCAG GCATTTGGGC
5221 ACAGAAGCAT TGACCCGATG GATGAAAATA CCACTGAAAA CATAAACGAC ACTTCATCA
5281 AAACCCTGCA GGGCCATGCC TTGAATTCCC TCACGAAAG CATGATGAA AACCTCCAAC
5341 GTATCATGAG ACCTCCAGTC TCCTCTAACT CAAAGACCGC TGCCTGGGTG ACAGAAGGGA
5401 TGTATTCTTT CTGCTACCGA GTGATGTTTG AAGCTGGGTA TTTAACTATC ACAGAAGGGA
5461 ATCTTACAAG GCGGACACA CAGAAAGCAC ATATTCTAAA CAATCTTGAC AACTTCAAGC
5521 AATTCGACAA AGTCTTT
```

FIG. 5A

```
   1 GAATTCTACT CTTTAAAGGG GTGAATATTA TGGTACTTGA ATTTATCTC AAGAAAATG
  61 AATAAAAAGT AACTAAATCA TTGAAAATAT CTGATGGCAT GGGTTTGTG GGGTAACTGG
 121 CATTCCACAG TGATTTTCAA AGGGCTTGTG CTGTTTTCAT TTTGCTTTGT TTTAGTTATG
 181 GAGCCCTTCC TTGAAACAAA CTTCATACTA CAGTCCTCTT TCATGAAGCA GAAGAGGCA
 241 GTGGGCAGAG CTCTCCTTTG GCTTTCTCCC CCACCACAAC AGGGAGCCCT GGAGCTCTAG
 301 GAGAGAAAAT CTGAAATATA AAGGCATGC ATGTGAGCTG TGGAGTCCCA GAGCCCTGGG
 361 TTTGCATCCT AGATCTGCAA CTCCCGTGAA TTGAGTTTTG GGAAGTTGCT GAAACTCTGA
 421 CCTCCTGTTT TCTCATGGTA TTGTGTAAG GGTTAAATGA GACAATGTAT GTGAAGACCC
 481 TGGCCCCACA GTAGAGGCTC TGCACACATT TCAGCCGATAC TTTCCTCATG TATTTCAAA
 541 AATGTTTCT CATTTTCTTA AAATGTCAGA AGAAGACAA CAGAACTTAC TTGCCTTTTA
 601 CAACAGAACA AATGAGCAA GTCAGAGGTC AAGGTGCTAA CATTCTTCAT GGTTCCTCAC
 661 CACCTTTTGT TCTGTTAGCC TATAGGGAAA AGTCTTCTTT CTCATCTCAT TATCTGCAGG
 721 GGAAAATAGT ACTTCAGCAA GTGATCCAGT TGAAGAACAT CTCCAGGGCC ATTAACATAC
 781 AGAGGTTTGT TCTACTCTCT CTGTGCTCCA TGTCTAAGAA CCTCAGCCTT CCTCCTAGGA
 841 GCTAGGGAAA GTCAGGAAAG TGAAAATAGT ACCCCAGCTA ATGAACTGCC CTGTGCTGGC
 901 CTGAGAAGAC AAGACCAGCT TCCTCAAGATT GGTTTCCTTC AATATGTCCT
 961 TTTGGAAATA TGTCCATGAC ATCGGAGAGA TAAAAGGAGC CAGGATTGCT CACATTCAGG
1021 AAAAAGCTC CACTATCTTT CTCTCTCTCC CCCTTCCCT CCCTCCCCCT GACTGCCCTC
1081 TTCTCTATCT CTCTCTCTCC CTGAGCTGGC AAGGTTAATT GGTCGCAGAA AGCCGAAGAA
1141 ACAAGTGGGC CTCCTGAAAC AAGTTCAAA AAGCCGAAA CGGGAAGAAA ACTACCACA
1201 AAAGTAAAGG CCTTCTTTGA AACCACTTAG TTCCAGGCCC CCAAGCCTGT CTTTAACTTG
```

FIG. 5B

```
1261 GATGAATGA GTTCTTCCTG TGCTACAGCA CCGCATAGTA GGGGCTGCCC TGGGCTGAA
1321 GCCAGAGCTT CACCATATTC AGTCATCTGT ACATTGAGGC AACAGTGCCT GCTTCATGGT
1381 GCTACCCTGT GGATTAAATG AAGCAAGTTT TTGATGATCT TGACACTGAA TATTGATGCA
1441 TTGGTCAGAC TTTTTCTGAT AGTAAAAAT GGTGGTTTCT TGTTGTCAGA AATCAAATCA
1501 ATATATTTGT TCTCCTGTTG ATTAGCTATG TCCCCTAGAG GGCAGGACT TTGCCTGTCT
1561 TATTTATCTC TGCATCTCCA GCACTTAAAA GGTGCCTTGC ATAAGGTACA TATTAAGTTC
1621 ATATGAATGA ATGAATGAAA TGCATATGAT TTATTCATAC CCAGTTGGTG GTGTGTTTAC
1681 CCTTTCCTAA ACCTGTAGTC AGATGGCCTT TGAATCCCCT GTACTTCTTG TGAGTACTG
1741 TGCTGTAAAG GTGACTATC ACACTTCAGT TCAGAGCAAT CTGGGCTTGA ATCCTGGATT
1801 TGCCAGTTTA TTAACTATAG CAAACATTTT TGAGCATACA TTGTGCCAAG TGCTAGGCTA
1861 ACTGTCTTAC ACACATTGTC TTATTCGTC TTATATCTA TGAGTCATGC ACTATAATCA
1921 TCCCATTTT ACAGATAAGA AAGCAAAGAC TTGGAGAGA AAAGCATCTT GTTCAAGGT
1981 AAATACTTAA TGGCCAAGCC AACATGCAAA TCTAGATTTA ATTGCAGCTT CCTCTTCATC
2041 TACCATTCGA ACTAATTCAA GCTATGTAAT ATTTCCCACT GAACCTTCTT GCCTCTACTT
2101 CCTTCATCTTT AACATGGTCA AAATACCTGT CCTGCCCAAG TTAGTTATTT CATTAAGTA
2161 GAAAAATACA AGAGAAGCTT TTAAAATGTG AAACCTCAAA TGAATGTAAA ATTATGATGA
2221 TTCCTTTAGA ATTTGTCAAC ACCTTCTTTT CTCTACTCCT GCTAGGCATT TACAATCTCA
2281 AAACCATGTA TTTAAGATGC AAAACTATAT TTGTATTTGC CATAACTGGT TTCTTTCCCT
2341 ATGGCTTCAT GAAAATGTGG CTCGAATGTG AAGCCCCAAA TTAATCAGA
2401 CAAGACTTCA CCAGCCCATT CCACAATAGA CTCCCATTAC TTTGCCCTGA CTTAGAAACC
2461 TCATATACAG TCTTGATTCA GTACAGCTCT GTGATGCTCT TGGAAATGC AAGTGCTTT
2521 CTTAATTGAG GCAATCTGTG TCCCACTACA GAGAGGTGGT TTAACTTGTG AATTC
```

FIG. 6A

```
   1  AGAGCAACCT GGGCAACATA GCAAACCCT  GTCTCTGCAA ACAATAAAA  GAAGAAAATT
  61  AGCTGGGTAT GGTGGCACAT GCTATAGTCG CAGCTACTCG AGAGGTTGAG GTGGAGGAT
 121  CAGTTCAGCC TGGGAGGTTG AGGCTGCAGT GAGCCAGATC ATGCCAGTGC ACTGCAGCAT
 181  GGGCAACAGA ATGAGACCCT GGCTAAAAGA AAACAAAATA AAAAATTCAG ACACAGGTTG
 241  AATCATTGAT AACAGCATAG TGGTAACAGA AAGAAAGTTT GGGAAATTTT TATCTGATCA
 301  GCTTCCCATA CCCTGTTCAT CTTTGTGTTA TGCACTGCCA GGCTGTCTGT AGTTCAGAC
 361  TCTATATCAT ATGACCTTCA AACACTTGGT TTGTTCTTCT CCTTCCTTCC TCCCTTCTTC
 421  TTTCATTTTT TATCTTTTTT TCTTTTAAAA TGTTTAGATA GTATAATAAG GAACTGCTGA
 481  GGCTTTCCAG TGCCCTCCTC AACATCCGGA CAGCTAAGGA GGATTTCACT TTGCACCTTG
 541  AGGACGGTTC CTACAACATC CGAAAAGATG ACATCATAGC TCTTTACCCA CAGTTAATGC
 601  ACTTAGATCC AGAAATCTAC CCAGACCCTT TGGTAAAGTC GCAGTGTGCC CGAATTGAAA
 661  TTCAATATCC AGTTGATAGC TACCTAGATC TAAATAAAGA GGAAATTTAC AATGGTAGAA
 721  TTGATTTTCT CATAGTAGTC ACAGGAATTG TCTGACTTAA TTGTGTTAAA TATTCATATA
 781  TTTTGAAAA TTTAGATAGT GGTCTCGAATT GTCCTGATAT TTGCCATCAC
 841  ACAGTCTTTG CTAGATTATA TTTGCAGTCA TGATAATAAA CCTGCCACTT TTTTTTCTT
 901  AAAAGCACC TCCTCCCAAA TCCAGGAAAT TGGAGGCTAA TATATTGATT ATTTCTAGTTT
 961  CTTCTGGAA CCCTTCTCTC TCTAGCTCTG CCTGACTAAG GAACTAATCG TTCAAGCAGG
1021  ATAGGAAGGT ATCACAAGC TTCCTTAGCT GCATTAAGCT CCTGTTCCTT ATTACTTTCT
1081  GATTCAATGT GGAGTATTTG CTAAATCACT AATGGGGTAG AATTAAAAAG AAAATTACTC
1141  TTTGGAGCTT CCAGGTTTAG AAAGAGATAA ATTTCTTTAA AACTAGCTTA AGGCGGTTT
```

FIG. 6B

```
1201 TCTTTGTATT TTTATTGCAG ACTTTTAAAT ATGATAGGTA TCTTGATGAA AACGGGAAGA
1261 CAAAGACTAC CTTCTATTGT AATGGACTCA AGTTAAAGTA TTACTACATG CCCTTTGAT
1321 CGGGAGCTAC AATATGTCCT GGAAGATTGT TCGCTATCCA CGAAATCAAG CAATTTTGA
1381 TTCTGATGCT TTCTTATTTT GAATTGGAGC TTATAGAGGG CCAAGCTAAA TGTCCACCTT
1441 TGGACCAGTC CCGGGCAGGC TTGGCATTT TGCCCGCCATT GAATGATATT GAATTAAAT
1501 ATAAATTCAA GCATTGTGA ATACATGGCT GGAATAAGAG GACACTAGAT ATTACAGGAC
1561 TGCAGAACAC CCTCACCACA CAGTCCCTTT GGACAAATGC ATTTAGTGGT GGCACCACAC
1621 AGTCCCTTTG GACAAATGCA TTTAGTGTG GTAGAAATGA TTCACCAGGT CCAATGTGT
1681 TCACCAGTGC TTGCTTGTGA AATCTTAACA TTTTGGTGAC AGTTTCCAGA TGCTATCACA
1741 GACTCTGCTA GTGAAAAGAA CTAGTTTCTA GGAGCACAAT AATTTGTTTT CATTTGTATA
1801 AGTCCATGAA TGTTCATATA GCCAGGGATT GAAGTTTATT ATTTTCAAAG GAAACACCTT
1861 TTATTTTATT TTTTTTCAA ATGAAGATAC ACATTACAGC CAGTGTGTGT AGCAGGCACC
1921 TGTAGTCTTA GCTACTCGAG AGGCCAAAGA AGGAGGATGC TTGAGCCCAG GAGTCAAGA
1981 CCAGCCTGA CAGCTTAGTG AGATCCCGTC TCCAAAGAAA AGATAIGTAT TCTAATTGGC
2041 AGATTGTTTT TTCCTAAGGA AACTGCTTTA TTTTTATAAA ACTGCCTGAC AATTATGAAA
2101 AAATGTTCAA ATTCACGTTC TAGTGAAACT GCATTATTTG TTGACTAGAT GGTGGGTTC
2161 TTCCGGTGTG ATCACGTTC ATAAGGATA TTTCAAATGT TATGATTAGT TATGTCTTTT
2221 AATAAAAAGG AAATATTTT CAACTTCTTC TATATCCAAA ATTCAGGGCT TTAAACATGA
2281 TTATCTTGAT TTCCAAAA CACTAAAGT GGTTTTT
```

FIG. 8

```
   1 AGTTTAACTT TAGTAAGGAG TCTAGACCAT GGCCAGGAGA AGGCAAACGG GTGAACCACC
  61 TCTAGAGAAT GGATTAATTC CATACCTGGG CTGTGCTCTG CAATTTGGTG CCAATCCTCT
 121 TGAGTTCCTC AGAGCAAATC AAAGGAAACA TGGTCATGTT TTTACCTGCA AACTAATGGG
 181 AAAATATGTC CATTTCATCA CAAATCCCTT GTCATACCAT AAGGTGTTGT GCCACGGAAA
 241 ATATTTTGAT TGGAAAAAAT TTCACTTTGC TACTTCTGCG AAGGCATTTG GGCACAGAAG
 301 CATTGACCCG ATGGATGGAA ATACCACTGA AAACATAAAC GACACTTTCA TCAAAACCCT
 361 GCAGGGCCAT GCCTTGAATT CCCTCACGGA AAGCATGATG GAAAACCTCC AACGTATCAT
 421 GAGACCTCCA GTCTCCTCTA ACTCAAAGAC CGCTGCCTGG GTGACAGAAG GGATGTATTC
 481 TTTCTGCTAC CGAGTGATGT TTGAAGCTGG GTATTTAACT ATCTTTGGCA GAGATCTTAC
 541 AAGGCGGGAC ACACAGAAAG CACATATTCT AAACAATCTT GACAACTTCA AGCAATTCGA
 601 CAAAGTCTTT CCAGCCCTGG TAGCAGGCCT CCCCATTCAC ATGTTCAGGA CTGCGCACAA
 661 TGCCCGGGAG AAACTGGCAG AGAGCTTGAG GCACGAGAAC CTCCAAAAGA GGGAAAGCAT
 721 CTCAGAACTG ATCAGCCTGC GCATGTTTCT CAATGACACT TTGTCCACCT TTGATGATCT
 781 GGAGAAGGCC AAGACACACC TCGTGGTCCT CTGGGCATCG CAAGCAAACA CCATTCCAGC
 841 GACTTTCTGG AGTTTATTTC AAATGATTAG GAACCCAGAA GCAATGAAAG CAGCTACTGA
 901 AGAAGTGAAA AGAACATTAG AGAATGCTGG TCAAAAAGTC AGCTTGGAAG GCAATCCTAT
 961 TTGTTTGAGT CAAGCAGAAC TGAATGACCT GCCAGTATTA GATAGTATAA TCAAGGAATC
1021 GCTGAGGCTT TCCAGTGCCT CCCTCAACAT CCGGACAGCT AAGGAGGATT TCACTTTGCA
1081 CCTTGAGGAC GGTTCCTACA ACATCCGAAA AGATGACATC ATAGCTCTTT ACCCACAGTT
1141 AATGCACTTA GATCCAGAAA TCTACCCAGA CCCTTTGACT TTTAAATATG ATAGGTATCT
1201 TGATGAAAAC GGGAAGACAA AGACTACCTT CTATTGTAAT GGACTCAAGT TAAAGTATTA
1261 CTACATGCCC TTTGGATCGG GAGCTACAAT ATGTCCTGGA AGATTGTTCG CTATCCACGA
1321 AATCAAGCAA TTTTTGATTC TGATGCTTTC TTATTTTGAA TTGGAGCTTA TAGAGGGCCA
1381 AGCTAAATGT CCACCTTTGG ACCAGTCCCG GCAGGCTTG GGCATTTTGC CGCCATTGAA
1441 TGATATTGAA TTTAAATATA AATTCAAGCA TTTGTGAATA CATGGCTGGA ATAAGAGGAC
1501 ACTAGATGAT ATTACGGCCA TGGC 3'
```

FIG. 11

```
  1 MARRRQTGEPPLENGLIPYLGCALQFGANP
 31 LEFLRANQRKHGHVFTCKLMGKYVHFITNP
 61 LSYHKVLCHGKYFDWKKFHFATSAKAFGHR
 91 SIDPMDGNTTENINDTFIKTLQGHALNSLT
121 ESMMENLQRIMRPPVSSNSKTAAWVTEGHY
151 SFCYRVMFEAGYLTIFGRDLTRRDTQKAHI
181 LNNLDNFKQFDKVPPALVAGLPIHMFRTAH
211 NAREKLAESLRHENLQKRESISELISLRMF
241 LNDTLSTFDDLEKAKTHLVVLWASQANTIP
271 ATFWSLFQMIRNPEAMKAATEEVKRTLENA
301 GQKVSLEGNPICLSQAELNDLPVLDSIKE
331 SLRLSSASLNIRTAKEDFTLHLEDGSYNIR
361 KDDIHALYPQLMHLDPEIYPDPLTFKYDRY
391 ICNGLRLKYYYMPFGSAT
421 ICPGRLFAHHEIKQFLIMLSYFELELIEG
451 QAKCPPLDQSRAGLGILPPLNDIEFKYKFK
481 HL*
```

GENOMIC DNA OF HUMAN CHOLESTEROL 7α-HYDROXYLASE AND METHODS FOR USING IT

This application is a continuation of application Ser. No. 08/361,458, filed Dec. 21, 1994, which is a continuation of Ser. No. 08/135,488, filed Oct. 13, 1993, abandoned.

Work related to subject matter described in this application was provided by research supported in part by NIH Grant GM 31584.

CROSS REFERENCE TO RELATED APPLICATIONS

U.S. Ser. No. 135,510 (Attorney Docket No. 18748/176 "TRUNCATED HUMAN CHOLESTEROL 7α-HYDROXYLASE, METHOD OF PRODUCTION AND USE THEREOF" to Chiang, J.; and U.S. Ser. No. 135,511 (Attorney Docket No. 18748/175) "CHOLESTEROL 7α-HYDROXYLASE GENE REGULATORY ELEMENTS AND METHODS FOR USING THEM" to Chiang, J. are both filed concurrently herewith and incorporated by reference in their entirety. Additionally, the present application is related to U.S. Ser. No. 08/361,458, filed Dec. 21, 1994, which is a continuation of U.S. Ser. No. 08/135,488, filed Oct. 13, 1993, and U.S. Ser. No. 08/187,453, filed Jan. 28, 1994.

BACKGROUND OF THE INVENTION

High serum cholesterol is commonly associated with an increased risk of heart-attack, atherosclerosis and circulatory disorders. In addition, a variety of diseases are caused by disorders of cholesterol catabolism, such as gallstone disease, atherosclerosis, hyperlipidemia and some lipid storage diseases.

The major pathway for disposal of cholesterol in the body is by secretion of cholesterol and bile acids into the gut. Bile contains free cholesterol and bile acids. The enzyme, cholesterol 7α-hydroxylase (CYP7), commits cholesterol to bile acid synthesis and catalyzes the first and rate-limiting step of bile acid synthesis in the liver hydroxylation of cholesterol at the 7α-position, thereby forming 7α-hydroxycholesterol. Thus, by increasing synthesis of bile acids, this enzyme plays a key role in the liver by depleting hepatic cholesterol pools, resulting in increased LDL uptake and a lowering of serum cholesterol levels.

Bile acids are physiological agents which are important in the solubilization of lipid-soluble vitamins, sterol and xenobiotics. Bile acids are synthesized exclusively in the liver and are secreted to the intestines where they are modified to secondary bile acids. Most bile acids are reabsorbed in the ileum and recirculated to the hepatocytes via the portal vein. The feedback of bile into the liver is known to inhibit cholesterol 7α-hydroxylase and thus inhibit the overall rate of bile acid synthesis. Cholesterol 7α-hydroxylase therefore has been a subject of intense investigations to elucidate the regulatory mechanisms of bile acid synthesis in the liver.

It is known that an interruption of bile acid reabsorption, such as that caused by the bile sequestrant, cholestyramine, or by a bile fistula, stimulates the rate of bile acid synthesis and cholesterol 7α-hydroxylase activity in the liver. It is believed that cholesterol 7α-hydroxylase activity in the liver is regulated primarily at the gene transcriptional level by bile acids, cholesterol, hormones, diurnal rhythm and other factors.

Generally, the regulation of eukaryotic genes is thought to occur at several locations, including the promoter sequences, which are located upstream of the transcription start site; enhancer or repressor sequences, which are located upstream of the promoter; within intron sequences, which are non-coding sequences located between exons or coding sequence; and in 3' sequences, which are located downstream from the coding region. The promoter sequence is unique to each gene and is required for the accurate and efficient initiation of gene transcription. Enhancers and/or repressors regulate promoter activity and determine the level of gene transcription during the development and differentiation of a particular tissue.

The promoter of most eukaryotic genes contains a canonical TATA box that binds a TFIID TATA box binding protein. TFIID complex and associated transcription activators (TAFs) interact with the basal initiation factors and RNA polymerase II to activate the promoter. The transcription complex assembly and initiation are regulated by transcription factors bound to enhancer elements located in the promoter and other regions of the gene (Pugh and Tjian, J. Biol. Chem. 267,679–682, 1992). Tissue-specific transcription factors and nuclear steroid hormone receptors are known to play an important role in the regulation of gene expression in different tissues during development and differentiation.

However, the mechanisms underlying the regulation of cholesterol 7α-hydroxylase gene expression at the molecular level are not understood. An understanding of the regulation of CYP7 gene expression would permit development of therapeutics for treating patients with defects in bile acid synthesis and cholesterol metabolism due to altered (deficient or excessive) gene expression.

In order to study the mechanism of regulation of human cholesterol 7α-hydroxylase at the molecular level, it is therefore important to determine the correct coding, non-coding and promoter region gene sequences. An elucidation of the enzyme's gene structure, a method for analyzing promoter and enhancer/repressor activity, as well as transgenic animal models with which to study human cholesterol 7α-hydroxylase, are desired. Attempts to provide a transgenic animal expressing recombinant CYP7 have not been successful using the cDNA of CYP7. Thus, important discoveries concerning the CYP7 gene and systems for studying the CYP7 enzyme's physiology, each of which aims towards the design of therapeutic drugs and the treatment of patients with defects in bile acid synthesis and cholesterol metabolism, are highly desired.

To understand the structure and function of human CYP7 and its regulation by factors, such as bile acids, cholesterol and hormones, it is essential to purify the human CYP7 enzyme. However, the CYP7 enzyme is present in an extremely low levels in human liver; therefore, it has not been possible to isolate sufficient quantities of purified, functional enzyme from human livers.

Although a cDNA molecule encoding human CYP7 enzyme has been determined, recombinant expression of human CYP7 has not heretofore been achieved. Karam and Chiang, Biochem. Biophys. Res. Commun. 185:588 (1992). Recently, a strategy to express a catalytically active, truncated rat cholesterol 7α-hydroxylase in E. coli was disclosed. Li and Chiang, J. Biol. Chem. 266 (29): 19186 (1991). The disclosures of both of those publications are expressly incorporated herein by reference. In the latter publication, it was disclosed that the expression of a membrane-bound hydrophobic protein in E. coli is difficult because the bacteria lacks internal membranes. Via PCR, a modified cDNA was generated that encoded a truncated enzyme lacking the N-terminal 23 amino acid residues of the rat cholesterol 7α-hydroxylase enzyme. The resulting protein was expressed, predominantly in the cytosol of the bacteria. The purified recombinant enzyme was active, as determined by its ability to hydroxylate cholesterol in a reconstituted system, and has a $K_m$ for cholesterol and $V_{max}$ similar to those of the rat microsomal (non-truncated) enzyme.

Despite the high sequence identity between the rat and human cholesterol 7α-hydroxylase, however, it previously has not been possible to express the human cholesterol 7α-hydroxylase in *E. coli* following the same strategy and using the same expression vector (pKK233-2) as that previously used for the expression of rat cholesterol 7α-hydroxylase. Thus, a catalytically active, recombinant human CYP7 enzyme is desirable. Recombinantly-expressed, truncated human CYP7 could be used to detect agents that stimulate or inhibit human CYP7's catalytic activity. Further, such recombinant protein can be used to produce anti-CYP7 antibodies which would be useful for screening assays, for example, to detect stimulated or inhibited production of human CYP7 in response to exposure of a compound to a human CYP7-producing culture.

SUMMARY OF THE INVENTION

An embodiment of the invention provides genomic DNA of cholesterol 7α-hydroxylase, in particular, DNA sequences of FIGS. 4, 5, and 6, clones λHG7α26 (ATCC 75534) and λHG7α5 (ATCC 75535), and fragments thereof.

Another embodiment provides an expression vector comprising genomic DNA of cholesterol 7α-hydroxylase and a host cell comprising the vector. Further, an expression vector can comprise a construct of a cholesterol 7α-hydroxylase promoter region operably linked to a reporter gene. Such a construct can be introduced into a mammal at an embryonic stage to provide a transgenic nonhuman mammal. Thereby, advantageously, germ cells and somatic cells of the mammal contain a promoter region from the human genomic CYP7 5' flanking sequence of the human cholesterol 7α-hydroxylase gene, wherein the promoter region is operably linked to a reporter gene.

The transgenic mammal described above containing the reporter construct can be used to screen or determine an agent's capacity to up- or down- regulate the promoter region of human cholesterol 7α-hydroxylase. This is achieved by exposing the mammal to a test agent and detecting an effect the expression of reporter gene in the mammal relative to that of a control, where no agent is applied. For example, when the mammal is exposed to agents that upregulate the promoter region of human cholesterol 7α-hydroxylase, expression of reporter gene is increased, and the agent is identified as potentially capable of decreasing serum cholesterol in humans.

Another embodiment of the invention provides a transformed cell comprising a recombinant human cholesterol 7α-hydroxylase gene which is operably linked to a cis-acting regulatory element that controls expression of said gene and wherein the recombinant human cholesterol 7α-hydroxylase gene sequence is substantially the same as the coding sequence of human cholesterol 7α-hydroxylase gene.

Another embodiment provides a cell, wherein transcription of recombinant human cholesterol 7α-hydroxylase gene is under the control of cis-acting regulatory elements/promoter that are the same as the sequences controlling the transcription of the endogenous human cholesterol 7α-hydroxylase gene, and wherein a cis-acting regulatory element controlling transcription of said gene is inducible.

Another object of the invention is to provide a cholesterol 7α-hydroxylase minigene for transforming an animal to produce functionally active cholesterol 7α-hydroxylase. A minigene of CYP7 in this context can comprise exons I through VI inclusive and at least two introns selected from the group consisting of I and II; and I, II and III. Optionally, the minigene can further comprise a CYP7 promoter region.

Another transgenic nonhuman mammal is provided according to the invention, the mammal having germ cells and somatic cells that comprise a recombinant human cholesterol 7α-hydroxylase gene that is operably linked to a cis-acting regulatory element that controls the expression of the gene in said mammal such that peripheral blood cholesterol levels and the production of bile acids in said mammal are affected. The gene is introduced into said the non-human mammal or an ancestor of the non-human mammal at an embryonic stage, and a chromosome of said mammal includes an endogenous coding sequence substantially the same as the coding sequence of the human cholesterol 7α-hydroxylase gene. Such a transgenic mammal is provided, wherein transcription of recombinant human cholesterol 7α-hydroxylase gene is under the control of those cis-acting regulatory elements/promoter sequences that control transcription of the endogenous human cholesterol 7α-hydroxylase gene, and wherein the cis-acting regulatory element controlling transcription of said gene is inducible.

Another embodiment of the invention provides catalytically active, truncated human cholesterol 7α-hydroxylase (CYP7). Advantageously, the truncated human CYP7, which can be produced recombinantly and in relatively large recoverable amounts, has a specific activity that is at least a substantial fraction of the specific activity of truncated rat enzyme produced in accordance with Li and Chiang, *J. Biol. Chem.* 266 (29): 19186 (1991).

Another embodiment of this invention provides a catalytically active, truncated human CYP7, which lacks a membrane anchor region that is present in human CYP7. Advantageously, amino acids 1 to 24 of the membrane anchor region are deleted.

Other embodiments provide analogs of the catalytically active, truncated human CYP7 proteins of this invention.

Another embodiment comprises a fusion protein comprising catalytically active, truncated human CYP7, or a portion thereof, and a structural protein in addition to the truncated human CYP7. Advantageously, the structural protein is capable of ready expression in a particular host system such that production of truncated human CYP7 can be increased by virtue of the increased production of the structural protein.

Other embodiments provide DNA encoding the foregoing catalytically active, truncated human CYP7 proteins.

Other embodiments of the invention provide an expression vector and a host cell useful for recombinant expression of catalytically active, truncated human CYP7.

Yet other embodiments provide a method for producing catalytically active, truncated human CYP7, comprising the step of culturing a host cell according to this invention under conditions which permit production of catalytically active truncated human CYP7.

Another embodiment provides an antibody which specifically recognizes an epitope of catalytically active, truncated human CYP7.

Another embodiment provides a method for screening a compound for its effect on expression of non-truncated human CYP7. The method comprises the steps of (a) providing a host cell according to the invention under conditions which permit production of catalytically active truncated human CYP7, (b) contacting the host cell with a compound and (c) detecting the amount of catalytically active, truncated human CYP7 expressed by the host cell.

Another embodiment provides a method for screening a compound for its effect on non-truncated human CYP7 enzyme activity. The method comprises the steps of (a) contacting catalytically active, truncated human CYP7 with a compound and (b) measuring the catalytic activity of the catalytically active, truncated human CYP7.

BRIEF DESCRIPTION OF THE DRAWINGS

FIG. 1A shows a gene map of the human CYP7 gene, while FIG. 1B and FIG. 1C show the gene map of clones λHG7α26 and λHG7α5, respectively. Exons I, II and III are represented by shaded boxes. Arrows indicate regions where sequences have been determined (shown in FIGS. 4, 5 and 6).

FIG. 3 (SEQ ID NO:8) shows a human CYP7 amino acid sequence that is expressed in a transgenic animal carrying a minigene.

FIGS. 4A–4F show (SEQ ID NO:9) a nucleotide sequence, including exon I, intron I, exon II, intron II and exon III, of human CYP7.

FIGS. 5A–5B show (SEQ ID N):10) a nucleotide sequence, including 5' upstream Eco RI fragment.

FIGS. 6A–6B show (SEQ ID NO:11) a nucleotide sequence, including intron IV exon V, intron V, and exon VI, of human CYP7.

FIG. 8 (SEQ ID NO:4) provides the cDNA sequence of human CYP7. The ATG start codon is located at positions 29–31 and the TGA stop codon at positions 1475–1477.

FIG. 11 (SEQ ID NO:5) provides the truncated human CYP7 amino acid sequence.

DESCRIPTION OF THE PREFERRED EMBODIMENTS

Figure 1:
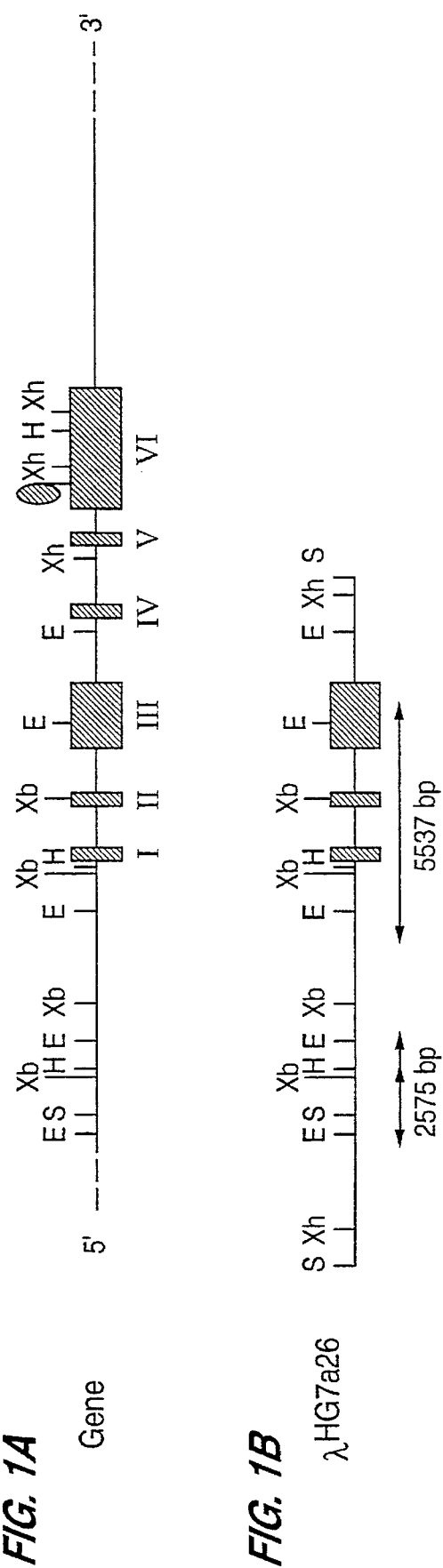

The present invention relates to the isolation and sequencing of the human genomic CYP7 gene, including intron and exon sequences and 5' upstream sequences. Two clones containing genomic CYP7 DNA are sequenced, as shown schematically in FIGS. 1B and 1C. The invention also includes a recombinant vector containing at least a fragment of the genomic CYP7 gene and a host cell, such as E. Coli, containing the vector.

The invention further includes "fragments" of the CYP7 genomic DNA, exemplified by a DNA fragment that is an exon or intron of the CYP7 gene. In FIGS. 4A–4F, exon I is nucleotides 2236 to 2319, intron I is 2320 to 3928, exon II is 3929 to 4169, intron II is 4170 to 5210, and exon III is 5211 to 5537. In FIGS. 6A–6B, partial exon IV is 1 to 456, exon V is 457 to 632, intron V is 633 to 1220, and exon VI begins at 1221 of FIGS. 6A–6B. The category of "fragment" within the present invention also encompasses any fragment obtained by digesting the disclosed DNA of the invention with any restriction endonucleases, preferably, at the restriction sites shown in FIG. 1. Other restriction fragments can be obtained as well, by using conventional skills in the art.

Also encompassed by the present invention are DNA sequences that hybridize under stringent conditions, preferably high stringent conditions, with any of the DNA sequences or fragments mentioned above. According to the present invention the term "stringent conditions" means conditions with a salt concentration of 4×SSC (NaCl-citrate buffer) at 62°–66° C., and "high stringent conditions" means conditions with a salt concentration of 0.1×SSC at 68° C.

From the determined gene sequence of human CYP7, a promoter region of the gene is further identified. Clone λHG7α26 contains an insert that spans about 8.0 kb of the 5'-upstream flanking sequence. According to the invention, this sequence information permits construction of a human CYP7 promoter operably linked to a reporter gene. This "promoter/reporter" gene construct is used to transform host cells and animals. For example, the promoter/reporter gene is used to transform E. coli strain JM101 or mammalian hepatocytes, or to transform a transgenic mouse or hamster.

In another embodiment of the invention, a transformed cell line or transgenic animal containing a promoter/reporter gene according to the invention is provided. Such a transformant readily detects an agent that increases or decreases expression of CYP7 gene. This is so because the agent's interaction with the CYP7 promoter region produces a corresponding reporter protein expression pattern that is easily detectable. For example, where the firefly-derived protein luciferase is used as a reporter gene, luciferase expression is measured quantitatively by its bioluminescence.

The CYP7 promoter region or certain regulatory elements excised therefrom can be used for the controlled expression of either the CYP7 gene or various reporter or indicator genes which allow quantitative determination of gene expression in the presence of inhibitory or stimulatory drugs. Reporter genes include, but are not limited to, E. coli β-galactosidase, galactokinase, interleukin 2, thymidine kinase, alkaline phosphatase, luciferase and chloramphenicol acetyltransferase (CAT). Such an expression system can, therefore, also be used for screening compounds for their ability to inhibit or stimulate expression of a structural gene.

In another embodiment, a minigene construct is provided by ligating a fragment of newly discovered genetic information, in particular a gene sequence excised from clone λHG7α26, together with a cDNA spanning exons 3–6. According to the present invention, a minigene is provided and used to transform an animal for in vivo production of human CYP7.

Figure 2:
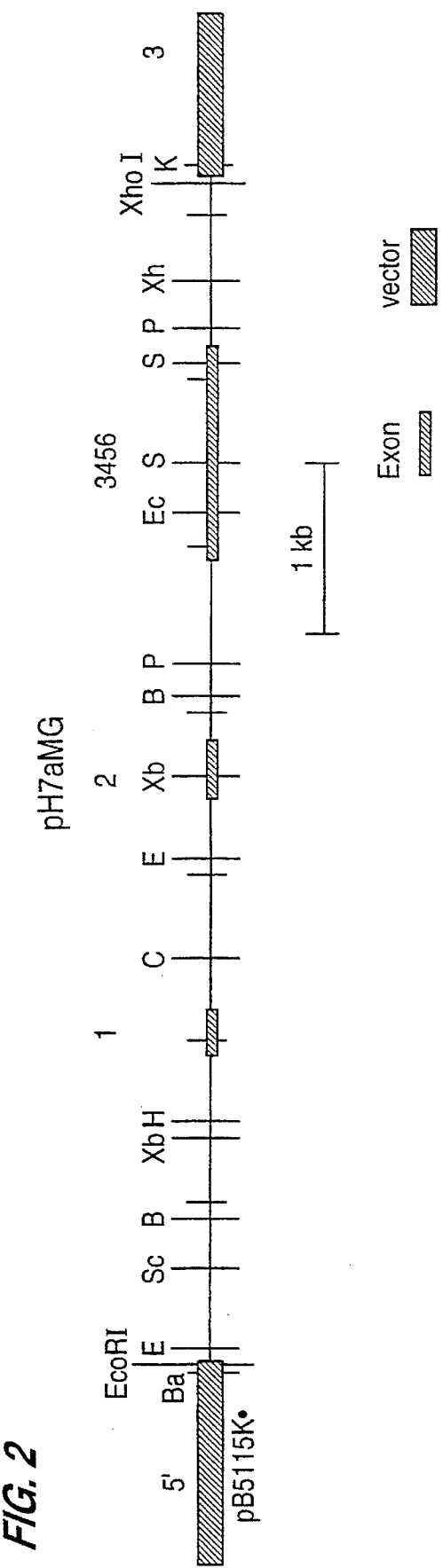
FIG. 2 is a diagrammatic representation of the construction of the human cholesterol 7α-hydroxylase containing plasmid, pH7aMG. Shaded thin boxes represent amino acid coding exons, while vector is represented by shaded thick boxes. A 5.5 kilobase EcoRI fragment (FIG. 4) which contains promoter region, exons I, II and partial exon III and introns I and II, was fused to a EcoRI-XhoI fragment of cDNA which contains partial exon III, exons IV, V and partial exon VI. An internal EcoRI site in exon III provided the linkage of the gene fragment to the cDNA to construct a minigene, as discussed in Example III. Restriction enzyme cleavage sites are as follows: Ba=BamH1, Ec=EcoR1, E=EcoR V, Sc=Sca 1, B=Bgl 11, Xb=Xba1, H=HinD111, C=Cla 1, P=Pst 1, Xh=Xho 1, S=Sma 1, K=Kpn 1.

In making a the minigene in accordance with the invention, a promoter region and exons I–VI are employed, as well as introns I and II, or introns I, II and III of the genomic CYP7 DNA. However, any of introns III, IV or V may be omitted. For example, introns III, IV and introns IV and V of the CYP7 gene can be omitted. Thus a preferred minigene according to the invention contains all of the CYP7 exons as well as introns I and II. Another minigene according to the invention contains all exons and introns I, II and III. Therefore, a method is provided for expressing a CYP7 gene in transgenic animals that have been transformed with a minigene, such as the minigene shown in FIG. 2.

Optionally the minigene can contain the promoter region of CYP7. Alternatively, another known promoter region is substituted for the promoter region of CYP7 to permit experimentally regulated promoter-driven expression in an animal. For example, a transgenic mouse can be made wherein the CYP7 minigene is driven by the metallothionein promoter. Use of this promoter in a transgenic mouse provides a model of CYP7 overexpression in the transgenic animal.

In another embodiment of the invention, a human CYP7 minigene permits production of a transgenic animal, preferably an animal that carries new genetic information in every tissue, including the germ cells. A minigene, when introduced into a transgenic animal, will express a CYP7 protein having an amino acid sequence shown in FIG. 3. This animal is a useful disease model for screening an agent in vivo effect on the regulation of CYP7 expression, as described further in Example 3.

Various methods are employed to introduce foreign genes into animals. These methods include: micro-injection of DNA into single cell embryos, retroviral infection of embryos and calcium phosphate-mediated DNA uptake by embryonic stem cells. Hogan et al., MANIPULATING THE MOUSE EMBRYO; A LABORATORY MANUAL (Cold Spring Harbor Laboratory, 1986); Leder et ai., U.S. Pat. No. 4,736,866; Leder et al., U.S. Pat. No. 5,175,383; Krimpenfort et al., U.S. Pat. No. 5,175,384, the contents of each of which are hereby incorporated by reference.

The most successful and most preferred technique is microinjection of DNA. Hammer et al., *J. Anim. Sci.* 63: 269 (1986); Gordon et al., *Science* 214: 1244 (1981); Brinster et al., *Proc. Natl. Acad. Sci. USA* 82: 4438 (1985). Microinjection involves the isolation of embryos at the single cell stage. The DNA encoding the gene of interest is microinjected in vitro into the isolated embryos and the manipulated embryos are implanted into pseudo-pregnant females. Transgenic animals can be identified shortly after birth by analyzing the DNA obtained from a tissue fragment, such as the tail, using probes specific for the inserted gene. Integration has been generally found to occur in a head-to-tail concatameric fashion at a single genomic site. Incorporation of the foreign gene at the one-celled stage results in a transgenic animal; if integration occurs at a multicellular stage, a mosaic results. Integration of two different embryonic stem cells may lead to the creation of a chimeric animal. Only microinjection results in the production of animals that can transmit the genetic information to their progeny in a Mendelian fashion. Germline integration is essential in order to utilize these transgenic animals as perpetual animal models.

Introduction of the recombinant human cholesterol 7α-hydroxylase gene at the fertilized oocyte stage ensures that the gene sequence will be present in all of the germ cells and somatic cells of the transgenic "founder" animal. The presence of the recombinant gene sequence in the germ cells of the transgenic founder animal means that approximately half of the founder animal's descendants will carry the activated recombinant gene sequence in all of their germ cells and somatic cells.

Several factors determine the level at which the new protein will be expressed, as well as its temporal and tissue-specific manner of expression. Perhaps the most important factors are the promoter and enhancer employed in controlling the expression of the protein encoded by the inserted DNA. Regulatory elements which are tissue-specific direct significant expression to a specific tissue; whereas ubiquitous promoters permit expression in different tissues within the animal.

Important cis-acting regulatory elements, other than the 5' upstream region, are required for expression of a human gene at levels equivalent to or higher than that in the unmodified organ. It is known that the first intron and second intron and possibly third intron of a human gene are important in the regulation of protein expression.

Furthermore, the presence of intronic sequences within the transgene have been shown to eliminate or at least dampen inhibitory effects of the site of DNA integration into the genome. Behringer et al., *Science* 245: 971 (1989); Lang et al., *EMBO J.* 7: 1675 (1988). For example, in order to overcome the positional effects of integration upon expression levels, the prior art has positioned enhancer regions 10–50 kb upstream, introns, or parts of introns close to splice junctions in the DNA constructs for transgenic animal production. Brinster et al., *Proc. Natl. Acad. Sci. USA* 85:836 (1988); Buchman et al., *Mol. Cell Biol.* 8:4395 (1988). Therefore, one of ordinary skill in this art, given the DNA sequence of the present invention, would be able to construct various combinations of cis-acting regulatory elements of the human cholesterol 7α-hydroxylase gene to test which regions are required for expression of the human gene at levels equivalent to or higher than that in the unmodified organ. The cis-acting regulatory elements of the human cholesterol 7α-hydroxylase gene to be used in such constructs are selected from: the 5' upstream region, the first intron, second intron and third intron of the human gene.

In general, the invention features a transgenic non-human vertebrate animal, preferably a mammal such as a rodent, eg., a mouse or hamster, containing germ cells and somatic cells that contain a recombinant gene which is substantially homologous with a vertebrate gene in the cholesterol 7α-hydroxylase family which is capable of expressing cholesterol 7α-hydroxylase. The recombinant gene is introduced into the animal, or an ancestor of the animal, at an embryonic stage, preferably the one-cell, or fertilized oocyte stage, and generally not later than about the 8-cell stage. The recombinant gene preferably is substantially homologous with (i.e., greater than 50% homologous, and preferably greater than 80% in terms of encoded amino acid sequence) human cholesterol 7α-hydroxylase.

Preferably, transcription of the human cholesterol 7α-hydroxylase encoding DNA is under the control of the promoter sequence that is the same as the promoter sequence controlling transcription of the endogenous coding sequence, so that the expressed protein is regulated similarly to its expression in humans. The term endogenous cis-acting regulatory elements refers to the nucleic acid sequence that controls the expression of a the human cholesterol 7α-hydroxylase gene in vivo.

The animals of the invention can be used as models to test for agents that potentially effect the expression of human cholesterol 7α-hydroxylase. The use of transgenic animals to test for agents that effect: (1) the expression of various enzymes involved in cholesterol metabolism and (2) atherosclerosis is well known to those of skill in the art, as described by Breslow, *Proc. Natl. Acad. Sci. USA* 90: 8314 (1993), the entire contents of which are hereby incorporated by reference. Since human cholesterol 7α-hydroxylase is the rate limiting enzyme controlling peripheral blood cholesterol levels, the consequent occurrence of hypercholesterolemia in humans is dependent upon the levels at which this enzyme is expressed. Hypercholesterolemia (or hypercholesteremia or hypercholesterinemia) is a clinical condition in which there is an abnormally large amount of cholesterol present in the cells and plasma of the circulating blood. Hypercholesterolemia is a serious medical condition that leads to atherosclerosis, atheromatous plaques, arteriole sclerotic plaque formation, hypertension and heart disease. The transgenic animals of the invention can be used for testing agents that may cure hypercholesterolemia, or relieve its symptoms, or for testing agents that may promote hypercholesterolemia.

The agents to be tested can be administered to an animal of the invention and the animal's peripheral cholesterol and bile acids are monitored. Peripheral cholesterol is measured by routine tests available in most clinical laboratories. Bile acid production is monitored using reverse phase high pressure liquid chromatography (HPLC).

Transgenic animals of the invention are most useful as animal models for testing agents and procedures that promote or inhibit overexpression or under expression of CYP7. Overexpression would result in increased bile acid synthesis from cholesterol whereas underexpression would result in decreased bile acid synthesis from cholesterol and hypercholesterolemia. Therefore, transgenic animals of the invention may be used to study the regulation of bile acid synthesis and hypercholesterolemia. In particular, a transgenic mouse or hamster on a high cholesterol diet is used to determine whether overexpression of CYP7 in the mice could prevent hypercholesterolemia. Transgenic mice fed a diet containing high levels of both bile acids and cholesterol are used to determine whether a high bile acid diet suppresses 7α-hydroxylase expression and thus induces hypercholesterolemia.

The constructs of the present invention may be used to assess gene expression in vitro as well as gene regulation in vivo. For example, the construct of FIG. 2 2 may be used to transfect hepatocytes and other mammalian cells to test for tissue specific expression of the CPY7 gene. Also, the construct of FIG. 7 may be used to transfect hepatocytes and other mammalian cells to assess the regulation of the CPY7 gene.

In general, the invention features a transformed mammalian cell, preferably a hepatocyte, containing a recombinant gene which is substantially homologous with a vertebrate gene in the cholesterol 7α-hydroxylase family which is capable of expressing cholesterol 7α-hydroxylase. The recombinant gene is introduced into the cell by various transfection means well known in the art. The recombinant gene preferably is substantially homologous with (i.e., greater than 50% homologous, and preferably greater than 80% in terms of encoded amino acid sequence) human cholesterol 7α-hydroxylase.

Preferably, transcription of the human cholesterol 7α-hydroxylase encoding DNA is under the control of the promoter sequence that is the same as the promoter sequence controlling transcription of the endogenous coding sequence, so that the expressed protein is regulated similarly to its expression in humans.

The cells of the invention can be used as models to test for agents that potentially effect the expression of human cholesterol 7α-hydroxylase. The agents to be tested can be provided to the cells and the expression of human cholesterol 7α-hydroxylase assayed. Such transformed cells are useful for testing agents that promote or inhibit overexpression or under expression of CYP7.

Analysis of the CYP7 promoter may be performed in cell culture using either the downstream recombinant CYP7 minigene or a reporter construct. The CYP7 regulatory elements can be used for the controlled expression of either the CYP7 gene or various reporter or indicator genes which allow quantitative determination of gene expression in the presence of inhibitory or stimulatory drugs. Reporter genes and systems have been described herein.

In another related discovery, it has been found surprisingly, that catalytically active, truncated human CYP7 now can be expressed recombinantly. This is achieved by using a bacterial strain having the characteristics of the *E. coli* strain TOPP3, and a vector having the characteristics of the expression vector pJL. No other bacteria strains or expression vectors have been found that possess the characteristics permitting expression of the truncated human CYP7 enzyme. In particular, "*E. Coli* TOPP3-pJL/H7α1.5" contains the expression vector pJL/H7α1.5 DNA and encodes a truncated human CYP7 cDNA that is expressed in relatively large amounts in the bacterial cytosol.

Therefore, one embodiment of the present invention is a catalytically active, truncated human CYP7 protein. "Truncated" as used herein means that a portion, all or substantially all of the complete membrane anchor region of human CYP7 has been deleted. Advantageously, all or a substantial portion of amino acids 1 to 24, which comprise the membrane anchor region in human CYP7, are deleted. FIG. 11 provides the amino acid sequence of a catalytically active, truncated human CYP7 protein in accordance with this invention.

By "catalytically active" it is meant that the CYP7 protein is capable of catalyzing, in the presence of reductase and a reducing agent such as NADPH, the initial hydroxylation of cholesterol at the 7α-position, thereby forming 7α-hydroxycholesterol. Catalytic activity can be measures in known assays using several well known parameters such as $K_M$ and $V_{Max}$. Advantageously, catalytic activity can be measured as specific activity and compared with the specific activity of the catalytically active, truncated rat CYP7 discussed above. Most advantageously, specific activity of the truncated human CYP7 and the truncated rat CYP7 are measured in simultaneously run assays under identical conditions. Otherwise, assay-to-assay variations in activity may be observed by virtue of differences in the assay conditions.

Also encompassed by the invention is an analog of catalytically active, truncated human CYP7. In accordance with this invention, the term "analog" includes a protein having conservative amino acids substitutions or deletions that do not eliminate the enzymatic activity of the truncated human CYP7. Advantageously, the analog retains a specific activity that is at least about ten percent (10%) of the specific activity of truncated rat CYP7 produced in accordance with Li and Chiang, *J. Biol. Chem.* 266: 19186 (1991).

Skilled artisans will readily appreciate that an analog of catalytically active, truncated human CYP7 having the amino acid sequence in FIG. 11 readily can be constructed. The analog can be the prepared, for example, by exploiting the degeneracy in the genetic code, or by effecting a point mutation which yields an amino acid substitutions and/or additions or deletions of non-essential amino acids. Advantageously, the amino acid substitutions can be conservative in accordance with well known principles.

By way of example, an analog advantageously includes those proteins having at least about 85%, and more advantageously at least about 90% amino acid sequence homology, which proteins still possesses substantially similar enzymatic activity as that of the truncated rat CYP7. Advantageously, the catalytically active, truncated human CYP7 or analog thereof will possess at least about 10%, advantageously at least about 25%, more advantageously at least about 50%, more advantageously at least about 75%, and more advantageously at least about 90% of the specific activity of catalytically active, truncated rat CYP7 as measured in simultaneous assays run under identical conditions.

The present invention further includes a fusion protein comprising catalytically active, truncated human CYP7, or a portion thereof, and a structural protein in addition to the truncated human CYP7. Advantageously, the structural protein is capable of ready expression in a particular host system. Advantageously, the structural protein is a protein which is produced in relatively high quantity by the host. In this way, production of truncated human CYP7 can be increased by virtue of the increased production of the structural protein. Thus a vector is provided that in addition to a truncated hCYP7 gene, such as H7α1.5, further contains a gene encoding at least one additional structural protein. The additional protein is advantageously selected from among proteins that are expressed at high levels in *E. coli*, including factor IX, for example. See Nagai et al., *Meth. Enzym.* 153:461 (1987), the contents of which are hereby expressly incorporated by reference.

Additional embodiments of this invention comprise DNAs which encode the proteins described herein. Those skilled in the art will appreciate that many different DNAs can encode a single protein, and preferred codons routinely can be employed for different expression systems. All such DNAs are contemplated within this invention. Further, within this embodiment are DNA sequences that hybridize under stringent conditions, preferably under highly stringent conditions, with the DNA sequence encoding catalytically active, truncated human CYP7. According to the present invention the term "stringent conditions" means hybridization conditions comprising a salt concentration of 4x SSC (NaCl-citrate buffer) at 62°–66° C., and "high stringent conditions" means hybridization conditions comprising a salt concentration of 0.1x SSC at 68° C.

Yet another embodiment of the invention provides a method of making catalytically active, truncated human CYP7 protein recombinantly. One method comprises culturing a host cell containing the gene encoding the protein or an analog thereof, advantageously *E. coli* TOPP3 (ATCC 69401), under conditions which permit production of the protein. Advantageously, the method further comprises the step of recovering quantities of protein. Advantageously, as discussed below, high quantities of the polypeptide are obtained. Skilled artisans will appreciate the various ways in which recombinant proteins of this invention can be prepared.

Compared to a corresponding amount of rat CYP7 produced according to Li and Chiang, *J. Biol. Chem.* 266: 19186 (1991), the level of truncated human CYP7 expressed according to the invention is increased substantially, i.e., by a four-fold increase in yield. According to the present invention, a method is provided for obtaining expression of at least 30 nmol human cholesterol 7α-hydroxylase in one liter of *E. coli* culture, but more advantageously, 50 nmol/liter. This markedly improved yield can be achieved by subcloning the cDNA in a pJL expression vector to form pJL/R7α1.5, which can then be transformed into *E. coli* strain TOPP3. The pJL expression vector is characterized by possessing (i) a transcription enhancer sequence, located upstream from and proximal to a ribosomal binding site, and (ii) an origin of replication for pUC12.

Another embodiment of this invention is an expression vector containing the DNA encoding truncated CYP7, especially an expression vector additionally containing a transcription enhancer region (T.E.), particularly wherein said T.E. is located upstream from and proximal to a ribosomal binding region. Preferably, the vector also has an origin of replication for pUC12 as well, or some other origin known to be associated with the expression of high copy numbers of an inserted gene. Typically, the T.E. and the ribosomal binding region are operably attached to the truncated CYP7 cDNA. An advantageous embodiment of the present invention includes the expression vector pJL/H7α1.5 containing DNA encoding truncated CYP7 and the transfected *E. coli* TOPP3 (ATCC 69401) as a host cell.

Also included is a method of making a truncated CYP7 protein that employs an expression vector containing a transcription enhancer region (T.E.), particularly wherein said T.E. is located upstream from and proximal to a ribosomal binding region and which preferably has an origin of replication for pUC12. This method can be exploited to make truncated CYP7 proteins having a species origin other than human or rat. Thus, for example, hamster, murine and other species of truncated CYP7 made by using an expression vector (without the human gene insert) and an *E. coli* TOPP3 host cell are encompassed by the invention. In particular, according to the present invention, *E. coli* TOPP3 transfected with a pJL expression vector containing a CYP7 genomic insert of the desired species of CYP7 is used to produce another species of truncated CYP7.

*E. coli* TOPP3-pJL/H7α1.5 was deposited on Aug. 25, 1993, at the American Type Culture Collection, ATCC, 12301 Parklawn Drive, Rockville, Md. 20852, U.S.A. under the accession number ATCC 69401.

Also included in the present invention are monoclonal and polyclonal antibodies, or binding fragments thereof, specific for truncated human CYP7, i.e., which specifically recognize an epitope of catalytically active, truncated human CYP7. Methods for the preparation of such antibodies are also contemplated (see Example 11 below). Further, an anti-truncated CYP7 antibody can be used in a method to screen compounds for their ability to inhibit or stimulate CYP7 enzyme expression (see Example 11). For example, either an antibody according to the invention or an antibody against non-truncated human CYP7 is used to detect the expression of truncated human CYP7 in an assay. Thus, to screen for an agent that enhances CYP7, an agent can be added to a culture of TOPP3-pJL/Hα1.5 for a period of time sufficient for the agent to modulate expression, after which expressed truncated human CYP7 is detected using any of the above-described antibodies in a Western blot. An increase in protein content, relative to the level of control enzyme expression from cells not exposed to the agent, detects an agent that stimulates expression of human CYP7. Results of such as assay optionally are confirmed with an in vivo transgenic animal assay, as described herein.

Truncated CYP7 obtained according to the present invention also can be used in a screening assay as an indicator of non-truncated CYP7 activity. A compound can be screened to determine whether it increases or decreases either the level of enzyme expression or its activity. A compound can be tested either alone or in the presence of physiological agents or drugs (see Examples 10 and 11). Information obtained can be used to screen for potentially beneficial drugs, and particularly for the design of drugs capable of treating patients with defects in bile acid synthesis and cholesterol metabolism.

A compound screening method according to the present invention can be performed as follows. To assess a compound's effect on CYP7 enzyme activity in human liver, the compound, in varying dosages, is tested in the enzyme assay method. Such a method, is advantageously performed on truncated CYP7, purified from *E. coli* TOPP3-pJL/H7α1.5. A method for detecting the enzyme's activity is described in Example 10 herein. A compound's effect on CYP7 enzyme levels is determined, for example, using a CYP7 specific antibody in a Western blot assay, as described in Example 11.

The following examples illustrate the invention and, as such, are not to be considered as limiting the invention set forth in the claims.

EXAMPLE 1

GENOMIC DNA OF CYP7 HUMAN CHOLESTEROL 7α-HYDROXYLASE

A human genomic library constructed with Sau3A1 partially digested human placental DNA ligated into a BamHI site of EMBL-3 Sp6/T7 phage vector (Clontech, Palo Alto, Calif.) was screened using a 1.6 kb EcoRI-PstI fragment of a human cholesterol 7α-hydroxylase cDNA isolated previously (Keram and Chiang, Biochem. Biophys. Res. Comm. 185, 588–595, 1992) as a hybridization probe. Hybridizations were carried out at a high stringent condition of 68° C., 1% SDS and 0.1x SSC. 800,000 pfu of phages were screened. After four cycles of screening, seven positive clones were plaque-purified. Three clones containing the largest inserts (λHG7α26, λHG7α5 and λHG7α52) were isolated and analyzed by restriction mapping. FIG. 1B shows the gene map of clone λHG7α26, which contains a 15 kb insert that spans about 8.0 kb of the 5'-upstream flanking sequence and exons I to III (FIGS. 4A–4F and 5A–5B). Clone λHG7α5 (FIG. 1C) contains intron IV, exon V, intron V and partial exon VI (FIGS. 6A–6B). An 8.0 kb 3'-flanking sequence extends beyond the sequenced region of λHG7α5 (FIG. 6).

Bacteriophage clones λHG7α26 and λHG7α5 both were deposited Aug. 25, 1993 at the American Type Culture Collection, ATCC, 12301 Parklawn Drive, Rockville, Md. 20852, USA under the accession numbers ATCC 75534 and ATCC 75535, respectively.

Five EcoRI fragments of the clone λHG26 were excised from the phage DNA insert by restriction digestion and shotgun subcloned into phagemid vector pBluescript II KS+ (Stratagene, La Jolla, Calif.). The clones were size-selected and EcoRI fragments were isolated from CsCl purified plasmids and used for sequencing. Nested deletions were generated by ExoIII/Mung Bean nuclease digestion according to manufacturer's instruction (Stratagene, Calif.) using the conditions of 37° C. incubation for 1 min intervals. This condition resulted in an average deletion of about 200 to 250 bp/min. DNA sequencing of the nested deletions were carried out by the dideoxy chain termination method using T7 sequenase version 2.0 (USB, Cleveland, Ohio) and $^{35}$S-dATP. Sequence data were obtained from both strands and the overlapping deletion clones and analyzed using DNASIS software (Hitachi America, Calif.).

Nucleotide sequences of a 5 kb EcoRI fragment and a 2.6 kb EcoRI fragments were determined. The 5 kb fragment contains the sequence from −1886 of the 5'-upstream region to partial exon 3 (FIGS. 4A–4F). Included in FIGS. 4A–4F is a 347 bp 3'-end sequence of a 3.5 Kb EcoRI fragment located immediately upstream of this 5 Kb fragment and a 233 bp 5' end sequence of a 2.6 kb EcoRI fragment immediately downstream of a 5 kb fragment. As shown in FIG. 1B, the 2.6 kb fragment (FIGS. 5A–5B) is located further 5' of the 3.5 kb EcoRI fragment. Thus, about 4875 bp of the 5'-upstream flanking region sequence of the gene were determined.

A comparison of sequences of the present invention to those of Molowa et al. (1992) in the overlapping region (1604 bp) revealed that sequences from the transcription start site to about −460 are identical; however, further upstream sequences vary significantly. A total of 52 sequence discrepancies were found, not all of are attributed to the presence of polymorphisms in the human genes. Cohen at al. (Genomics, 14, 153–161, 1992) reported a 723 bp upstream sequence. Seven mismatches in Cohen's sequence from +1 to −723 were identified. A "T" to "C" conversion at nucleotide -469 was identified to be a Mae II polymorphism (Thompson et al., Biochem. Biophys. Acta. 1168, 239–242, 1993). The 5'-flanking sequence of the present invention was identical to that reported by Thompson et al., (1993), with the exception of a mismatch at nucleotide −1197, found in the overlapping region from 1 to nucleotide −2235. No intron sequences have been reported by other laboratories.

Clone λHG7α5 was also sequenced from the 5' end of the gene. FIGS. 6A–6B is the 2316 basepair sequence that contains partial intron IV, exon V, intron V and exon VI of the human CYP7 gene.

EXAMPLE 2

PROMOTER/REPORTER TRANSGENIC ANIMAL

Figure 7:
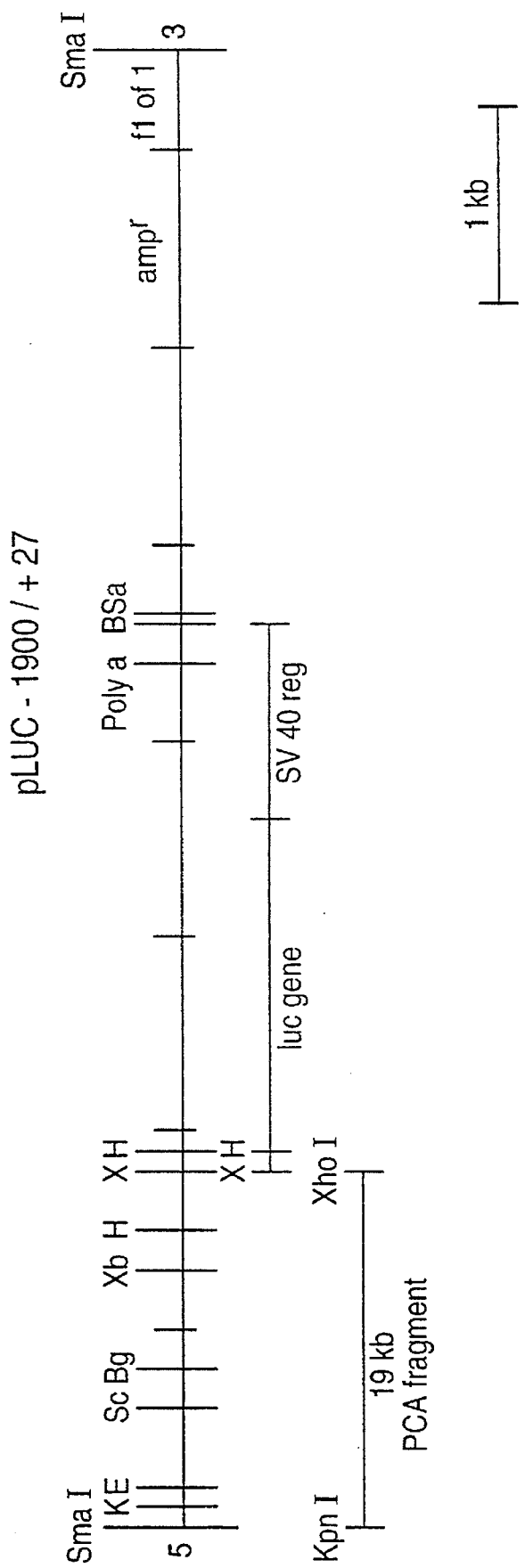
FIG. 7 is a diagramatic representation of the construction of the luciferase reporter gene vector that includes the 5' sequence from the human genomic cholesterol 7α-hydroxylase gene, and the reporter luciferase gene described in Example 2. Restriction enzyme cleavage sites are as follows: K=Kpn 1, E=EcoR1, Sc=Sca 1, Bg=Bgl 11, Xb=Xba 1, H=Hind 111, X=Xho 1, B=BamH 1, Sa=Sal 1.

Assessment of gene regulation in transgenic animals using the luciferase reporter system is well known to those of skill in the art. DiLelia et al., *Nucl. Acids. Res.* 16: 4159 (1988), incorporated by reference in its entirety. Vectors for producing such reporter constructs are commercially available from Promega Corporation (2800 Woods Hollow Road, Madison Wis. 53711-5399). For example, the pGL2-Basic luciferase vector (Promega) may be used to construct a cassette that will report the important cis-acting elements in the CYP7 5' sequence from the human genomic cholesterol 7α-hydroxylase gene. As shown in FIG. 7, a 1.9 kb promoter region of the human genomic clone HG7a26 from −1879 to +24, which is equivalent to nucleotides 2236 through 4139 of FIGS. 4A–4F, was obtained by PCR amplification. A Kpn 1 site was introduced at the 5' end using an HLU-1 primer (HLU-1 primer= 5'TACCGCTCGAGTGATTAGAAAGGGAAGGAT 3') (SEQ ID NO:6) and an Xho 1 site was introduced at the 3' end using an HLU-2 primer (HLU-2 primer= 5'CAAGAATGATAGATAAAAT 3') (SEQ ID NO:7). This recombinant Kpn 1-Xho 1 fragment containing the human cholesterol 7α-hydroxylase promoter region was ligated into the luciferase vector pGL2-Basic (Promega), which had been cut with restriction enzymes Kpn 1 and Xho. The resulting promoter-luciferase reporter chimeric construct was purified and used to transform host cells, such the E. coli strain JM101.

The entire 1.9 kb human cholesterol 7α-hydroxylase promoter region and luciferase reporter gene, including a poly(A) signal, is flanked by unique Kpn 1 and BamH 1 restriction enzymes sites. The Kpn 1 and BamH1 fragment is 4.6 kb and is used for microinjection into fertilized oocytes in the production of transgenic animals. Transgenic animals containing this construct, as assayed by Southern Blot analysis, are then tested for various agents which are capable of upregulating or downregulating the CYP7 cis acting elements. Alternatively, given the DNA sequence of the present invention, one of skill in the art is able to contruct various combinations of cis-acting regulatory elements of the human cholesterol 7α-hydroxylase gene to test the specific regions and positional affects that are required for expression of the human cholesterol 7α-hydroxylase gene at levels equivalent to or higher than that in the unmodified organ. The cis-acting regulatory elements of the human cholesterol 7α-hydroxylase gene to be used in such constructs are selected from: the 5' upstream region, the first intron, second intron and third intron of the human gene.

Tissue samples, including liver, are tested for luciferase activity by methods well known in the art. *Promega Notes* 28:1 (1990); *Promega Technical Bulletin* (Promega Corporation, September 1993); Wood, BIOILLUMINESCENCE AND CHEMILUMINESCENCE (John Wiley and Sons, 1991). Briefly, the homogenized tissue supernatants are mixed with luciferin and Coenzyme A in a buffer containing ATP. Luciferin illuminescence, as detected using a luminometer, only occurs in the presence of the recombinant luciferase expressed in the transgenic tissue.

EXAMPLE 3

PRODUCTION & ANALYSIS OF TRANSGENIC MICE CONTAINING DNA ENCODING HUMAN GENOMIC CHOLESTEROL 7A-HYDROXYLASE

The recombinant CYP7 minigene present in the pH7aMG vector is incorporated into the germ cells of mice as follows: The construction of the pH7aMG shown diagrammatically in FIG. 2. The entire 7.2 kb insert in pH7aMG can be removed by restriction enzyme cleavage with BamH 1 and Kpn 1. The CYP7 minigene DNA was prepared for injection by digestion with 4 units each of BamH1 and Kpn1 per ug of DNA per I hour at 37° C., electrophoresed through a 1% agarose gel, and purified as described by Sinn et al., *Cell* 49: 465 (1987). The isolated 7.2 kb DNA fragment was injected into the pronuclei of fertilized one-cell mouse or hamster eggs derived from the FVB/NHd inbred strain (Taconic laboratory, Germantown, N.J.). About 100 to 1000 copies of linearized plasmid is incorporated per pronucleus. Following microinjection, viable eggs are transferred to the oviducts of pseudopregnant Swiss Webster mice (Taconic Farms), as described by Wagner et al., *Proc. Natl. Acad. Sci. USA* 78:5016 91981). Mice are housed in an environmentally controlled facility maintained on a 10 hour dark: 14 hour light cycle. The eggs in the foster females are allowed to develop to term.

Between two and six weeks of age, the DNA of each pup born is analyzed by Southern hybridization using DNA taken from the pup's tail. DNA is extracted from 1.5 cm tail sections. Davis et al. *Meth. Enzym.* 65:405 (1980). The nucleic acid pellet is resuspended in 200 μl of 10 mM Tris-Cl pH 7.4, 0.1 mM EDTA, and 10 μg is digested with Kpn1 and BamH1, electrophoresed through 1.0% agarose, and transferred to nitrocellulose. Southern, *J. Mol. Biol.* 98:503 (1975). Filters are hybridized overnight to CYP7 transgene specific probe in the presence of 10% dextran sulfate and washed twice in 2X SSC, 0.1% SDS at 64° C. A CYP7 transgene specific probe is a fragment of the CYP7 minigene that will not hybridize to related sequences in the host genome. This fragment is free of repetitive sequences. The CYP7 transgene specific probe is labeled with $^{32}$P dCTP by nick translation. Rigby et al., *J. Mol. Biol.* 113:237 (1977).

Southern hybridization indicates which founder mice retain the CYP7 minigene construct.

3.1 Transcription of the Human Cholesterol 7α-hydroxylase Minigene in Transgenic Mice Transcription of the newly acquired gene in tissues was determined by extracting RNA from the tissues and assaying the RNA by Northern Blot analysis. The excised tissue is rinsed in 5.0 ml cold Hank's buffered saline and total RNA is isolated by methods employing a CsCl gradient. Chirgwin et al. *Biochem.* 18:5294 (1979). RNA pellets are washed twice by reprecipitation in ethanol and quantitated by absorbance at 260 nm. Single stranded, uniformly labeled RNA probe is prepared using a transgene specific probe. Such a transgene specific probe is a fragment of the CYP7 minigene that will not hybridize to related sequences in the host genome. This fragment is free of repetitive sequences. Since the human cholesterol 7α-hydroxylase mRNA is 3 kb and the endogenous mouse cholesterol 7α-hydroxylase mRNA is 4 kb, even the entire CYP7 minigene construct cut out of the pH71MG could be used to identify the presence of the transcribed exogenous human cholesterol 7α-hydroxylase gene. Melton et al., *Nucl. Acids Res.* 12:7035 (1984).

To test for transcription of the CYP7 minigene, labelled single-stranded probe fragments are isolated on 8M urea 5% acrylamide gels, electroeluted and hybridized to total RNA. Berk et al., *Cell* 12: 721 (1977). The hybridization mixture contains 50,000 CPM to 100,000 cpm of probe (Specific Activity - $10^8$ cpm/ug), 10 μg total cellular RNA, 50% formamide, 500 mM NaCl, 20 mM Tris pH 7.5, 1 mM EDTA. Melton et al. (1984) supra. Hybridization temperatures vary according to the GC content. The hybridizations are terminated by the addition of 1500 units of RNAase A and RNAase T$_1$ (Sigma, St. Louis, Mo.). RNAase digestions are carried out at 37° C. for 15 minutes. The samples are then ethanol precipitated and electrophoresed on 8M urea 5% acrylamide gels.

The tissues analyzed are liver, muscle, pancreas, stomach, brain, intestines, eye, aorta, salivary gland and kidney. 10 μg of total RNA from each of these tissues is analyzed using a transgene specific probe.

In situ hybridization, using the transgene specific probe, of the histologic sites that transcribe the CYP7 minigene confirm the presence of the exogenous cholesterol 7α-hydroxylase gene in the transcribing tissues.

3.2 Localization of Transgene Expression mRNA transcripts are evaluated in liver RNA (prepared as above) after conversion to cDNA, PCR amplification and Southern hybridization analysis. Rosenfeld et al., supra. To ensure that CYP7 transgene is specifically evaluated and that the 5' and 3' portion of mRNA transcripts are present, two separate primer pairs are used: a 5' primer pair to detect the 5' end of recombinant construct mRNA transcripts and a CYP7-specific antisense primer, and a 3' primer pair to evaluate the 3' end of the recombinant mRNA transcript. Fiers et al., *Nature* 273: 113 (1978)

PCR amplification products are evaluated by agarose gel electrophoresis followed by Southern hybridization using $^{32}$P-labeled human CYP7 probes.

Northern analysis of liver RNA from transgenic animals will exhibit CYP7 directed human mRNA transcripts of a size similar to that directed by these constructs in cultured cells. Levels of a constituitively expressed protein transcripts, such as Beta-actin or glyceraldehyde-3-phosphate dehydrogenase, serve as a positive control and are normally similar for both transgenic and nontransgenic tissue samples.

3.3 Expression of Recombinant Human Cholesterol 7α-hydroxylase in Transgenic Animal Tissues Expression of the human cholesterol 7α-hydroxylase transgene is evaluated by Western Blotting or immunohistochemistry. Alternatively, expression of a linked reporter gene, such as luciferase or LAC-Z, may be used to quantitate the tissues or cells expressing the transgene. For western blot or immunohistochemical detection of transgenically expressed protein, antibodies specific for human cholesterol 7α-hydroxylase are used to detect the presence of this enzyme in various tissue sections or protein preparations from various tissues. Antibodies specific for human cholesterol 7α-hydroxylase are described in J. Chiang (Attorney docket 18748/176, U.S. Ser. No. 08/135,510). Briefly, 1 mg purified CYP7 enzyme is mixed with an equal volume of Freund's adjuvant and 5 mg/ml of heat-killed microbacteria. The emulsified antigen mixtures were injected on the back of New Zealand white rabbits by intradermal injections on multiple sites. After six weeks, 0.5 mg of purified human enzyme was mixed with incomplete adjuvant and used for booster injections to the same rabbits. Six weeks later, blood samples were collected from ear veins and tested for the presence of antibodies by Ouchterlony double diffusion and by immunoblotting as described previously by Chiang, et al., *J. Biol. Chem.* 265, 3889–3897 (1990), incorporated by reference in its entirety. For immunoblot analysis, one µg of purified human CYP7 enzyme was loaded on a 7.5 % SDS-polyacrylamide gel, separated polypeptides were electrophoretically transferred to an Immobilon P membrane by a modified procedure reported previously (Chiang et ai., supra. (1990)). Diluted antisera were reacted with membrane and subsequently reacted with second antibody, anti-rabbit IgG conjugated with alkaline phosphatase, and then stained with nitroblue tetrazolium (NBT) and 5-bromo-4-chloro-3-indolylphosphate (DCIP) as described previously.

The presence of human 7 alpha-hydroxylase expression in tissues is evaluated by immunohistochemistry using a human 7 alpha-hydroxylase specific antibody. The alkaline phosphatase monoclonal anti-alkaline phosphatase method is used to detect binding of the specific antibody to various tissue sections.

EXAMPLE 4

ANIMAL TESTING

Transgenic animals of the invention are most useful as animal models for testing agents and procedures that promote or inhibit overexpression or under expression of CYP7. The CYP7 expressing animals are tested for materials that are suspected of promoting or inhibiting hypercholesterolemia. The animals are exposed to various dosages of a known agent and tested for peripheral blood cholesterol and bile acid production. Animals and their descendants that have either increased or decreased peripheral blood cholesterol levels are then tested for the effect of an agent on the expression of CYP7.

Transgenic animals treated with agents that cause overexpression of CYP7 are used to study whether such overexpression prevents hypercholesterolemia when such treated animals are on a high cholesterol diet. Also, transgenic mice fed a diet containing high levels of both bile acids and cholesterol are used to determine whether a high bile acid diet suppresses 7α-hydroxylase and thus induces hypercholesterolemia.

EXAMPLE 5

TISSUE CULTURE OF TRANSGENIC CELL LINES

The transgenic animals of the invention can be used as a source of cells for cell culture. Cells of the tissues of the transgenic animal that contain the activated recombinant gene can be cultures, using standard tissue culture techniques and used, for example to study the causes of hypercholesterolemia at the cellular and tissue level.

EXAMPLE 6

PRODUCTION OF TRANSFORMED CELLS: PROMOTER/REPORTER GENE CONSTRUCTS

Assessment of gene regulation in transformed mammalian cells using the luciferase reporter system is well known to those of skill in the art. deWet et al., *Mol. Cell. Biol.* 7: 725 (1987). The same pGL2-Basic luciferase vector (Promega) constructs described for the transgenic animals may be used in vitro. Also, luciferase activity in cell culture is performed by methods well known in the art. *Promega Notes* 28:1 (1990); *Promega Technical Bulletin* (Promega Corporation, September 1993). Briefly, the supernatants of lysed cells are mixed with luciferin and Coenzyme A in a buffer containing ATP. Luciferin illuminescence, as detected using a luminometer, only occurs in the presence of the recombinant luciferase expressed in the transformed cells.

The transformed promoter-reporter cells of the invention can be used as models to test for agents that potentially effect the expression of human cholesterol 7α-hydroxylase.

To determine the promoter sequences responsible for regulation of cholesterol 7α-hydroxylase, deletions of the human CYP7 cis-acting elements are ligated upstream of the luciferase reporter gene (Luc). The promoter fragments were generated by the polymerase chain reaction using the primers and a human CYP7 genomic clone as the template. The fragments were blunted by filling in with the Klenow fragment of DNA polymerase and then digested with Xho I. The fragments were then ligated into pGL2-basic vector (Promega) which had been digested with SmaI and Xho I, and transformed into E. coli HB101 cells. The resulting plasmids could be used to transfect primary hepatocytes or hepatoma cells for the study of human luciferase gene expression under the control of the human CYP7 promoter.

Chloramphenicol acetyltransferase (CAT) reporter gene constructs were made by using the polymerase chain reaction and primers to amplify the 5' flanking regions and introns 1, 2 and 3 of the human CYP7 gene. Fragments are ligated into a promoterless pCAT basic vector (Promega). This plasmid is then used to generate nested deletions containing various pieces of 5' flanking DNA, intron 1, intron 2 and/or intron 3.

EXAMPLE 7

PRODUCTION OF TRANSFORMED CELLS: MINIGENE CONSTRUCTS

The DNA of each transformed cell line from each construct is analyzed by Southern hybridization. DNA is extracted from the cells culture and the nucleic acid pellet is resuspended in 200 ul of 10mMTris-Cl pH 7.4, 0.1 mM EDTA, and 10 ug is digested with Kpn1 and BamH1, electrophoresed through 1.0% agarose, and transferred to nitrocellulose. Southern, J. Mol. Biol. 98:503 91975). Filters are hybridized overnight to CYP7 transgene specific probe in the presence of 10% dextran sulfate and washed twice in 2X SSC, 0.1% SDS at 64° C. A CYP7 transgene specific probe is a fragment of the CYP7 minigene that will not hybridize to related sequences in the host genome. This fragment is free of repetitive sequences. The CYP7 transgene specific probe is labeled with $^{32}$p dCTP by nick translation. Rigby et al., J. Mol. Biol. 113:237 (1977). Southern hybridization indicates cell lines contain the CYP7 minigene construct.

Transcription of the newly acquired gene in cultured cells is determined by extracting RNA from the cells and assaying the RNA by Northern Blot analysis, as described above.

Expression of recombinant human cholesterol 7α-hydroxylase in cell culture is evaluated by Western Blotting or immunocytochemistry. Alternatively, expression of a linked reporter gene, such as luciferase or LAC-Z, may be used to quantitate the tissues or cells expressing the transgene. For western blot or immunocytochemical detection of the recombinant protein, antibodies specific for human cholesterol 7α-hydroxylase are used to detect the presence of this enzyme in the various transformed cells.
In Vitro Agent Testing Transformed cell lines of the invention are most useful as in vitro models for testing agents and procedures that promote or inhibit overexpression or under expression of CYP7. The CYP7 expressing cell lines are tested for materials that are suspected of promoting or inhibiting hypercholesterolemia. The cells are exposed to various dosages of a known agent and tested for the presence of human cholesterol 7α-hydroxylase.

EXAMPLE 8

PRODUCTION AND EXPRESSION OF TRUNCATED HUMAN CHOLESTEROL 7α-HYDROXYLASE IN E. COLI

Figure 9:
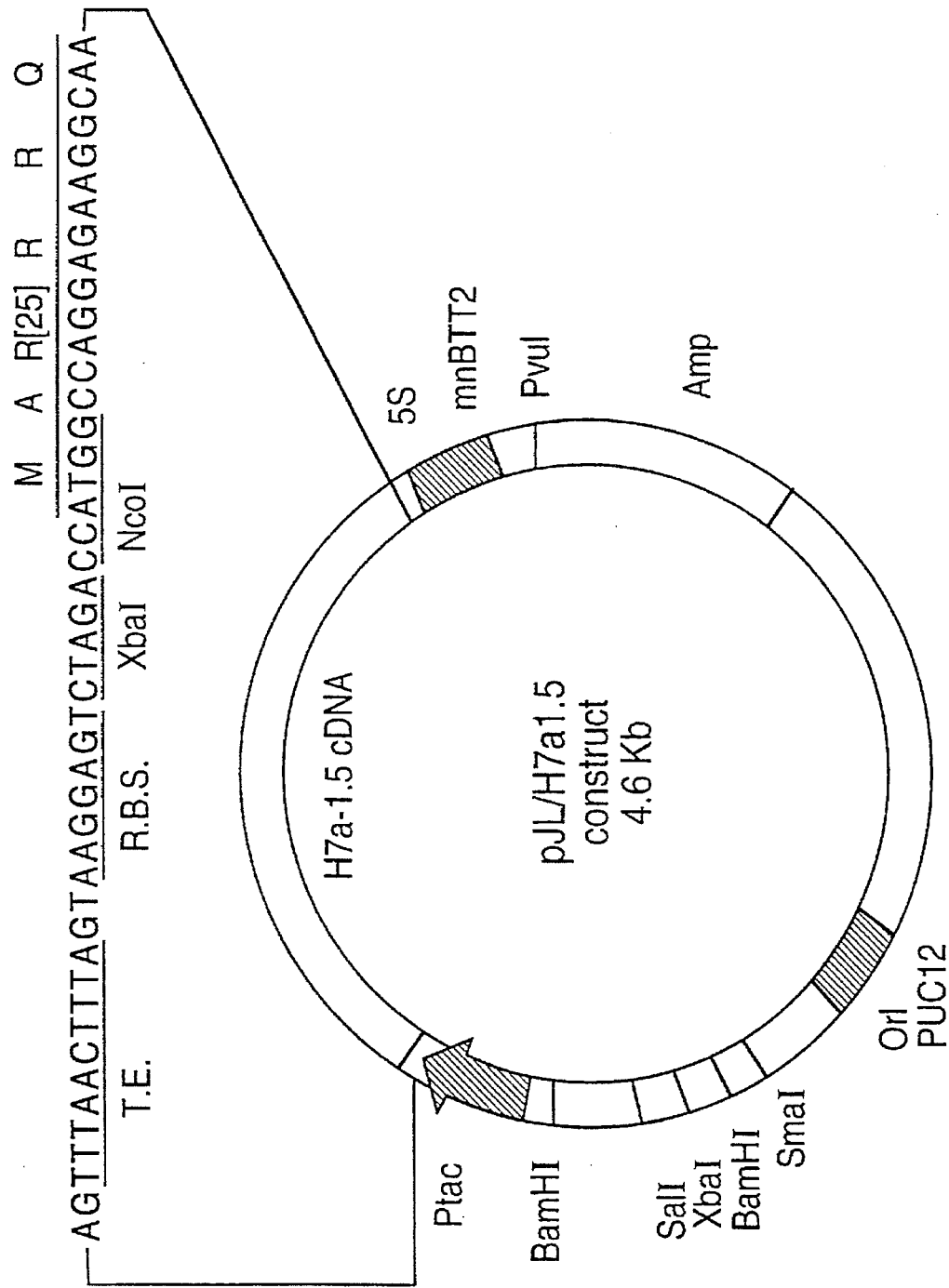
FIG. 9 illustrates a recombinant expression vector construct for truncated human cholesterol 7α-hydroxylase cDNA. Nucleotides 1–46 of SEQ ID NO:4 are also shown in this Figure. The PCR-generated cDNA, H7α1.5, was inserted in an NcoI digested expression vector pJL, as described in Example 1. Abbreviations are as follows: Transcription enhancer (T.E.), ribosome binding site (R.B.S.), Xba I and NcoI (restriction enzyme sites), M (methionine), A (alanine), R[25] (arginine, residue 25 of full-length protein); G (glutamine). In the vector, restriction enzyme sites, the ampicillin resistance gene (Amp), the origin of replication of PUC12 (Ori PUC12) and the tac promoter (ptac) are indicated.

Two primers were designed for the generation of a truncated human cholesterol 7α-hydroxylase cDNA by polymerase chain reaction using the full length human clone PHC7F as the template. Karam and Chiang, Biochem. Biophys. Res. Commun. 185:588–95 (1992). The 5'-primer had a sequence of 5'GCCATGGCCAGGAGAAGGCAAACGGGT-3, which encoded an N-terminus with a sequence of Met-Ala-Arg(25)-Arg(26)-Arg(27)-Glu(28), etc. The 3'-primer had a sequence (SEQ ID NO:1) of GCCATGGCCGTAATATCATCTAG-3,' which was complementary to the cDNA sequence (SEQ ID NO:2) from 1599 to 1612 near the 3'-end of the coding region. The cDNA generated was sequenced to confirm the human sequence (SEQ ID NO:3) (FIG. 8). This cDNA was ligated to the Nco I site (GCCATG) of the pJL plasmid. The recombinant construct, pJL/H7α1.5 (FIG. 9), was then transformed into a battery of bacteria strains.

It was found that the TOPP3 strain of E. coli harboring pJL/H7 α1.5 was capable of expressing truncated human cholesterol 7α-hydroxylase in very high amounts. Bacteria carrying pJL/H7α1.5 were cultured in "Terrific" broth containing 100 µg/ml ampicillin for 6 hours. One (1) mM IPTG was added to induce the production of protein at 30° C. for 15 to 18 hours. Addition of 2 mM δ-aminolevulinic acid in the culture increased the expression level by 100%. About 20 nmol of human cholesterol 7α-hydroxylase were expressed per liter of culture.

EXAMPLE 9

PURIFICATION OF THE BACTERIALLY EXPRESSED HUMAN CHOLESTEROL 7α-HYDROXYLASES

Culturing the bacteria carrying the recombinant vector encoding truncated human CYP7 was performed by inoculating 8 liters of Terrific broth containing 100 µg/ml ampicillin with a 6-hour culture of TOPP3-pJL/H7α1.5. This culture was grown at 37° C. until the O.D.$_{600}$ reached from about 0.4 to about 0.6, which occurred in about 3 hours. IPTG was added to a final concentration of 1 mM and incubation was carried out at 30° C. for 15 to 18 hours.

After induction, the cultures were harvested by centrifugation at 5,000 rpm for ten minutes at 4° C. The cells were then resuspended in 1/100 volume of buffer A (100 mM potassium phosphate, pH 7.4, 0.5% sodium cholate, 20% glycerol, 0.1 mM EDTA, 0.1 mM DTT and 0.5 mM PMSF). The cells were then lysed in buffer A with 200 µg/ml lysozyme. The supernatant was collected after spinning down the total lysate at 100,000×g for one (1) hour at 4° C. The pellet was resuspended thoroughly in the same buffer and centrifuged again. Both supernatants were combined and stored on ice overnight after the addition of 100 units of DNaseI. The clear lysate was then applied to an Octylamino Sepharose 4B column (2.6×15 cm). This column was washed and eluted with the same buffer. The eluted fractions were dialyzed against buffer B (10 mM potassium phosphate, pH 7.4, 0.2% sodium cholate, 0.2% Emulgen 911, 0.1 mM EDTA, 0.05 mM DTT, 0.5 mM phenyl methyl sufonyl fluoride (PMSF)), applied to a hydroxyapatite column (2.4×7 cm) and equilibrated with the same buffer. This column was then washed with 200 ml of 10 mM potassium phosphate buffer, then with 150 ml of 50 mM potassium phosphate buffer and then eluted with 300 ml of 100 mM potassium phosphate buffer. These three buffers also contained 20% glycerol, 0.3% sodium cholate, 0.05 mM EDTA, 0.1 mM DTT and 0.5 mM PMSF. The purified sample was brought to 0.2% Emulgen 911 and then dialyzed against 10 mM potassium phosphate buffer, pH 7.4, 20% glycerol, 0.1 mM EDTA, 0.1 mM DTT, 0.5 mM PMSF and 0.2% Emulgen 911 (buffer C). The sample was then applied to a second hydroxylapatite column (0.5×3.0 cm) equilibrated with buffer C and eluted with buffer C but containing 360 mM potassium phosphate. At this stage, the purity of the human cholesterol 7α-hydroxylase was confirmed by SDS-polyacrylamide gel electrophoresis.

EXAMPLE 10

CHARACTERIZATION OF THE PURIFIED HUMAN CHOLESTEROL 7α-HYDROXYLASE

The truncated enzyme was purified from recombinant bacteria. Purification methodology is described by Li and Chiang, *J. Biol. Chem.* 266 (29): 19186 (1991), the contents of which are expressly incorporated by reference herein in its entirety. The activity of CYP7, in both the presence and absence of the compound, is measured as described by Chiang, *Meth. Enzym.* 206:483 (1991), the contents of which is expressly incorporated by reference herein in its entirety.

Purified truncated enzyme was active in the reconstitution of cholesterol 7α-hydroxylase activity in the presence of NADPH-cytochrome P450 reductase and phospholipid (purified CYP7 enzyme (0.1 nmoles), 2 units of NADPH-cytochrome P450 reductase, 40 µg/ml of L-dilauroyl-glyceryl-3-phosphorylcholine, 100 µM cholesterol in 10 µl of 45% Molecusol, 0.015% CHAPS (3-((3-cholamidopropyl) dimethylaminio)-1-propanesulfonate), 0.1M potassium phosphate, pH 7.4, 1 mM EDTA, 5 mM DTT and 0.1% Emulgen 911). The addition of Molecusol, at varying concentrations, stimulated activity by three-fold. The reaction was started by the addition of 1 mM NADPH and proceeded for 20 minutes, at 37° C. Reactions were terminated by adding 0.8% sodium cholate. Products were oxidized by adding 1 unit of cholesterol oxidase and incubated at 37° C. for 10 minutes. The reaction mixture was extracted three (3) times with 6 ml each of petroleum ether and combined extracts were dissolved in 100 µl of acetonitrile: methanol (70:30; v/v) and analyzed on a C18 reverse-phase HPLC column as described previously. Chiang, *Meth. in Enzymol.* 206:483–91 (1991).

Figure 10:
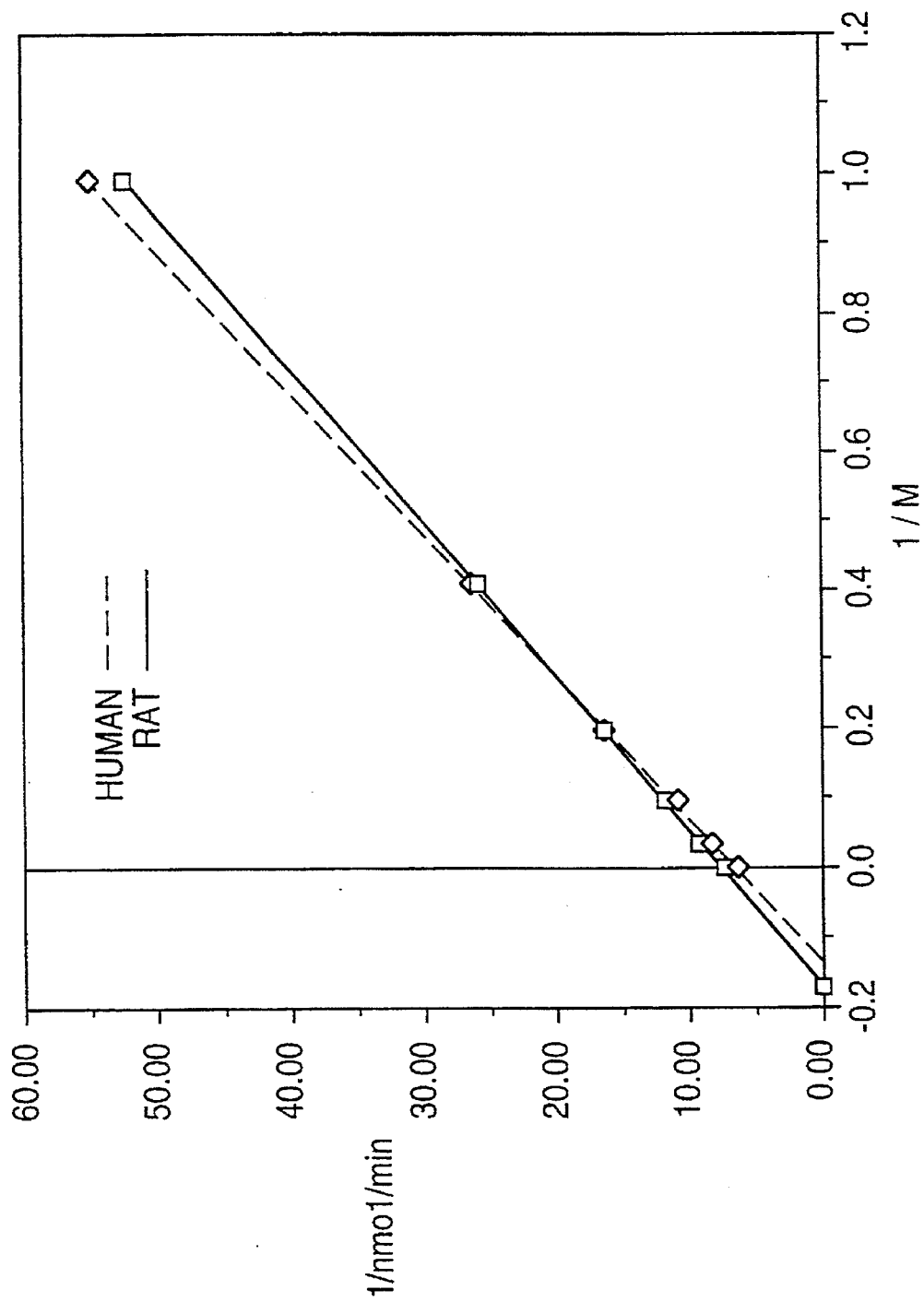
FIG. 10 illustrates a Lineweaver-Burke plot of activities of truncated human and truncated rat cholesterol 7α-hydroxylase in E. coli. Truncated CYP7 activity was measured using a reconstitution assay, such as that described in Example 10, at different concentrations of cholesterol, as indicated. Linear regression was used to draw the line.

The $K_m$ and $V_{max}$ for cholesterol have been determined in comparison with the truncated, bacterially expressed rat CYP7 enzyme (FIG. 10). The $K_m$ for the truncated human enzyme was 5.85 µM and $V_{max}$ was 0.13 nmol/min, which were similar to those of the truncated, bacterially expressed rat enzyme and of intact enzyme isolated from rat liver microsomes. Thus, the isolated truncated human CYP7 enzyme has similar kinetic properties to the truncated rat CYP7 enzyme.

EXAMPLE 11

ASSAY FOR SCREENING COMPOUNDS FOR ABILITY TO INHIBIT OR STIMULATE NON-TRUNCATED CYP7 ENZYME ACTIVITY IN HUMAN LIVER.

A. Preparation of Antibodies Against the Purified Human Cholesterol 7α-Hydroxylase As mentioned above, an assay system using antibodies raised against purified, truncated human CYP7 is used to screen compounds for their ability to inhibit or stimulate non-truncated CYP7 enzyme activity in human liver. Antibodies to truncated human CYP7 can be produced as follows.

One (1) mg purified truncated CYP7 enzyme was mixed with an equal volume of Freund's adjuvant and 5 mg/ml of heat-killed microbacteria. The emulsified antigen mixtures were injected on the back of New Zealand white rabbits by intradermal injections on multiple sites. After six (6) weeks, 0.5 mg of purified human enzyme was mixed with incomplete adjuvant and used for booster injections to the same rabbits. Six (6) weeks later, blood samples were collected from ear veins and tested for the presence of antibodies by Ouchterlony double diffusion and by immunoblotting as described previously by Chiang et al., *J. Biol. Chem.* 265:3889–97 (1990), incorporated by reference in its entirety.

For a Western Blot analysis, one (1) µg of purified human CYP7 enzyme was loaded on a 7.5% SDS-polyacrylamide gel, separated polypeptides were electrophoretically transferred to an Immobilon P membrane by a modified procedure reported previously. Chiang et al., supra. (1990). Diluted antisera were reacted with membrane and subsequently reacted with second antibody, anti-rabbit IgG conjugated with alkaline phosphatase, and then stained with nitroblue tetrazolium (NBT) and 5-bromo-4-chloro-3-indolylphosphate (DCIP) as described previously.

B. Assay Using Antibodies Against the Purified Human Cholesterol 7α-Hydroxylase

The specific antibody described above can be used in a screen assay to measure the inhibitory or stimulatory effects of a particular compound on the expression of CYP7 in human liver by a corresponding analysis of the effect on truncated CYP7. To quantitate the amount of expressed truncated enzyme in Western Blot analysis, such as described immediately above, varying concentrations of purified truncated human CYP7 enzyme, from 1 to 10 µgs, are run on adjacent lanes on the 7.5% SDS-polyacrylamide gel to those lanes containing the human CYP7 enzyme from the experimentally treated cells. A stimulation of truncated CYP7 expression is detected by a darker band, relative to control, on the Western blot. If a compound stimulates CYP7 enzyme expression and/or activity, then such an agent or drug could potentially be used to reduce cholesterol in humans. If an agent or drug inhibits CYP7 enzyme expression and/or activity, then such a compound should be used with caution because it potentially could increase serum cholesterol levels in humans.

---

What is claimed is:

1. A method for screening a compound for its effect on expression of non-truncated human CYP7 cholesterol 7α-hydroxylase (CYP7), comprising the steps of:

(a) providing a host cell having the characteristics of *E. coli* TOPP3, wherein said host cell contains an expression vector comprising DNA encoding catalytically active, truncated human CYP7, under conditions which permit production of catalytically active truncated human CYP7;

(b) contacting said host cell with a compound; and (c) detecting the amount of the catalytically active, truncated human CYP7 expressed by the host cell.

2. A method according to claim 1, wherein said compound is a physiological agent derived from the human body.

3. A method according to claim 1, wherein said compound is a physiological agent derived from a source other than the human body.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GCCATGGCCA GGAGAAGGCA AACGGGT                                    2 7
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:2:

Met Ala Arg Arg Arg Glu
   1                5

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCATGGCCG TAATATCATC TAG                                                       23

( 2 ) INFORMATION FOR SEQ ID NO:4:

( i ) SEQUENCE CHARACTERISTICS:
        ( A ) LENGTH: 1524 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

```
AGTTTAACTT  TAGTAAGGAG  TCTAGACCAT  GGCCAGGAGA  AGGCAAACGG  GTGAACCACC    60
TCTAGAGAAT  GGATTAATTC  CATACCTGGG  CTGTGCTCTG  CAATTTGGTG  CCAATCCTCT   120
TGAGTTCCTC  AGAGCAAATC  AAAGGAAACA  TGGTCATGTT  TTTACCTGCA  AACTAATGGG   180
AAAATATGTC  CATTTCATCA  CAAATCCCTT  GTCATACCAT  AAGGTGTTGT  GCCACGGAAA   240
ATATTTTGAT  TGGAAAAAAT  TTCACTTTGC  TACTTCTGCG  AAGGCATTTG  GCACAGAAG    300
CATTGACCCG  ATGGATGGAA  ATACCACTGA  AAACATAAAC  GACACTTTCA  TCAAAACCCT   360
GCAGGGCCAT  GCCTTGAATT  CCCTCACGGA  AAGCATGATG  GAAACCTCC   AACGTATCAT   420
GAGACCTCCA  GTCTCCTCTA  ACTCAAAGAC  CGCTGCCTGG  GTGACAGAAG  GGATGTATTC   480
TTTCTGCTAC  CGAGTGATGT  TGAAGCTGG   GTATTAACT   ATCTTTGGCA  GAGATCTTAC   540
AAGGCGGGAC  ACACAGAAAG  CACATATTCT  AAACAATCTT  GACAACTTCA  AGCAATTCGA   600
CAAAGTCTTT  CCAGCCCTGG  TAGCAGGCCT  CCCCATTCAC  ATGTTCAGGA  CTGCGCACAA   660
TGCCCGGGAG  AAACTGGCAG  AGAGCTTGAG  GCACGAGAAC  CTCCAAAAGA  GGGAAAGCAT   720
CTCAGAACTG  ATCAGCCTGC  GCATGTTTCT  CAATGACACT  TTGTCCACCT  TGATGATCT    780
GGAGAAGGCC  AAGACACACC  TCGTGGTCCT  CTGGGCATCG  CAAGCAAACA  CCATTCCAGC   840
GACTTTCTGG  AGTTTATTTC  AAATGATTAG  GAACCAGAA   GCAATGAAAG  CAGCTACTGA   900
AGAAGTGAAA  AGAACATTAG  AGAATGCTGG  TCAAAAAGTC  AGCTTGGAAG  GCAATCCTAT   960
TTGTTTGAGT  CAAGCAGAAC  TGAATGACCT  GCCAGTATTA  GATAGTATAA  TCAAGGAATC  1020
GCTGAGGCTT  TCCAGTGCCT  CCCTCAACAT  CCGGACAGCT  AAGGAGGATT  TCACTTTGCA  1080
CCTTGAGGAC  GGTTCCTACA  ACATCCGAAA  AGATGACATC  ATAGCTCTTT  ACCCACAGTT  1140
AATGCACTTA  GATCCAGAAA  TCTACCCAGA  CCCTTTGACT  TTTAAATATG  ATAGGTATCT  1200
TGATGAAAAC  GGGAAGACAA  AGACTACCTT  CTATTGTAAT  GGACTCAAGT  TAAAGTATTA  1260
CTACATGCCC  TTTGGATCGG  GAGCTACAAT  ATGTCCTGGA  AGATTGTTCG  CTATCCACGA  1320
```

```
AATCAAGCAA TTTTTGATTC TGATGCTTTC TTATTTTGAA TTGGAGCTTA TAGAGGGCCA      1380

AGCTAAATGT CCACCTTTGG ACCAGTCCCG GGCAGGCTTG GGCATTTTGC CGCCATTGAA      1440

TGATATTGAA TTTAAATATA AATTCAAGCA TTTGTGAATA CATGGCTGGA ATAAGAGGAC      1500

ACTAGATGAT ATTACGGCCA TGGC                                            1524
```

( 2 ) INFORMATION FOR SEQ ID NO:5:

( i ) SEQUENCE CHARACTERISTICS:
        ( A ) LENGTH: 482 amino acids
        ( B ) TYPE: amino acid
        ( D ) TOPOLOGY: linear ( x i ) SEQUENCE DESCRIPTION: SEQ ID NO:5:

```
Met Ala Arg Arg Arg Gln Thr Gly Glu Pro Pro Leu Glu Asn Gly Leu
 1               5                  10                  15

Ile Pro Tyr Leu Gly Cys Ala Leu Gln Phe Gly Ala Asn Pro Leu Glu
            20                  25                  30

Phe Leu Arg Ala Asn Gln Arg Lys His Gly His Val Phe Thr Cys Lys
        35                  40                  45

Leu Met Gly Lys Tyr Val His Phe Ile Thr Asn Pro Leu Ser Tyr His
    50                  55                  60

Lys Val Leu Cys His Gly Lys Tyr Phe Asp Trp Lys Lys Phe His Phe
65                  70                  75                  80

Ala Thr Ser Ala Lys Ala Phe Gly His Arg Ser Ile Asp Pro Met Asp
                85                  90                  95

Gly Asn Thr Thr Glu Asn Ile Asn Asp Thr Phe Ile Lys Thr Leu Gln
            100                 105                 110

Gly His Ala Leu Asn Ser Leu Thr Glu Ser Met Met Glu Asn Leu Gln
        115                 120                 125

Arg Ile Met Arg Pro Pro Val Ser Ser Asn Ser Lys Thr Ala Ala Trp
    130                 135                 140

Val Thr Glu Gly Met Tyr Ser Phe Cys Tyr Arg Val Met Phe Glu Ala
145                 150                 155                 160

Gly Tyr Leu Thr Ile Phe Gly Arg Asp Leu Thr Arg Arg Asp Thr Gln
                165                 170                 175

Lys Ala His Ile Leu Asn Asn Leu Asp Asn Phe Lys Gln Phe Asp Lys
            180                 185                 190

Val Phe Pro Ala Leu Val Ala Gly Leu Pro Ile His Met Phe Arg Thr
        195                 200                 205

Ala His Asn Ala Arg Glu Lys Leu Ala Glu Ser Leu Arg His Glu Asn
    210                 215                 220

Leu Gln Lys Arg Glu Ser Ile Ser Glu Leu Ile Ser Leu Arg Met Phe
225                 230                 235                 240

Leu Asn Asp Thr Leu Ser Thr Phe Asp Asp Leu Glu Lys Ala Lys Thr
                245                 250                 255

His Leu Val Val Leu Trp Ala Ser Gln Ala Asn Thr Ile Pro Ala Thr
            260                 265                 270

Phe Trp Ser Leu Phe Gln Met Ile Arg Asn Pro Glu Ala Met Lys Ala
        275                 280                 285

Ala Thr Glu Glu Val Lys Arg Thr Leu Glu Asn Ala Gly Gln Lys Val
    290                 295                 300

Ser Leu Glu Gly Asn Pro Ile Cys Leu Ser Gln Ala Glu Leu Asn Asp
305                 310                 315                 320

Leu Pro Val Leu Asp Ser Ile Ile Lys Glu Ser Leu Arg Leu Ser Ser
```

|     |     |     |     | 325 |     |     |     |     | 330 |     |     |     |     | 335 |     |
|-----|-----|-----|-----|-----|-----|-----|-----|-----|-----|-----|-----|-----|-----|-----|-----|
| Ala | Ser | Leu | Asn | Ile | Arg | Thr | Ala | Lys | Glu | Asp | Phe | Thr | Leu | His | Leu |
|     |     |     | 340 |     |     |     | 345 |     |     |     |     | 350 |     |     |     |
| Glu | Asp | Gly | Ser | Tyr | Asn | Ile | Arg | Lys | Asp | Asp | Ile | Ile | Ala | Leu | Tyr |
|     |     | 355 |     |     |     | 360 |     |     |     |     | 365 |     |     |     |     |
| Pro | Gln | Leu | Met | His | Leu | Asp | Pro | Glu | Ile | Tyr | Pro | Asp | Pro | Leu | Thr |
|     | 370 |     |     |     |     | 375 |     |     |     |     | 380 |     |     |     |     |
| Phe | Lys | Tyr | Asp | Arg | Tyr | Leu | Asp | Glu | Asn | Gly | Lys | Thr | Lys | Thr | Thr |
| 385 |     |     |     |     | 390 |     |     |     |     | 395 |     |     |     |     | 400 |
| Phe | Tyr | Cys | Asn | Gly | Leu | Lys | Leu | Lys | Tyr | Tyr | Met | Pro | Phe | Gly |     |
|     |     |     |     | 405 |     |     |     | 410 |     |     |     |     | 415 |     |     |
| Ser | Gly | Ala | Thr | Ile | Cys | Pro | Gly | Arg | Leu | Phe | Ala | Ile | His | Glu | Ile |
|     |     |     | 420 |     |     |     | 425 |     |     |     |     | 430 |     |     |     |
| Lys | Gln | Phe | Leu | Ile | Leu | Met | Leu | Ser | Tyr | Phe | Glu | Leu | Glu | Leu | Ile |
|     |     | 435 |     |     |     | 440 |     |     |     |     | 445 |     |     |     |     |
| Glu | Gly | Gln | Ala | Lys | Cys | Pro | Pro | Leu | Asp | Gln | Ser | Arg | Ala | Gly | Leu |
|     | 450 |     |     |     | 455 |     |     |     |     | 460 |     |     |     |     |     |
| Gly | Ile | Leu | Pro | Pro | Leu | Asn | Asp | Ile | Glu | Phe | Lys | Tyr | Lys | Phe | Lys |
| 465 |     |     |     | 470 |     |     |     |     | 475 |     |     |     |     |     | 480 |
| His | Leu |     |     |     |     |     |     |     |     |     |     |     |     |     |     |

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TACCGCTCGA GTGATTAGAA AGGGAAGGAT                        30

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CAAGAATGAT AGATAAAAT                                    19

( 2 ) INFORMATION FOR SEQ ID NO:8:

( i ) SEQUENCE CHARACTERISTICS:
        ( A ) LENGTH: 504 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Met | Thr | Thr | Ser | Leu | Ile | Trp | Gly | Ile | Ala | Ile | Ala | Ala | Cys | Cys |
| 1   |     |     |     | 5   |     |     |     |     | 10  |     |     |     |     | 15  |     |
| Cys | Leu | Trp | Leu | Ile | Leu | Gly | Ile | Arg | Arg | Arg | Gln | Thr | Gly | Glu | Pro |
|     |     |     | 20  |     |     |     |     | 25  |     |     |     |     | 30  |     |     |

```
Pro Leu Glu Asn Gly Leu Ile Pro Tyr Leu Gly Cys Ala Leu Gln Phe
         35                  40                  45
Gly Ala Asn Pro Leu Glu Phe Leu Arg Ala Asn Gln Arg Lys His Gly
         50                  55                  60
His Val Phe Thr Cys Lys Leu Met Gly Lys Tyr Val His Phe Ile Thr
 65                  70                  75                  80
Asn Pro Leu Ser Tyr His Lys Val Leu Cys His Gly Lys Tyr Phe Asp
                 85                  90                  95
Trp Lys Lys Phe His Phe Ala Thr Ser Ala Lys Ala Phe Gly His Arg
             100                 105                 110
Ser Ile Asp Pro Met Asp Gly Asn Thr Thr Glu Asn Ile Asn Asp Thr
         115                 120                 125
Phe Ile Lys Thr Leu Gln Gly His Ala Leu Asn Ser Leu Thr Glu Ser
    130                 135                 140
Met Met Glu Asn Leu Gln Arg Ile Met Arg Pro Pro Val Ser Ser Asn
145                 150                 155                 160
Ser Lys Thr Ala Ala Trp Val Thr Glu Gly Met Tyr Ser Phe Cys Tyr
                 165                 170                 175
Arg Val Met Phe Glu Ala Gly Tyr Leu Thr Ile Phe Gly Arg Asp Leu
             180                 185                 190
Thr Arg Arg Asp Thr Gln Lys Ala His Ile Leu Asn Asn Leu Asp Asn
         195                 200                 205
Phe Lys Gln Phe Asp Lys Val Phe Pro Ala Leu Val Ala Gly Leu Pro
    210                 215                 220
Ile His Met Phe Arg Thr Ala His Asn Ala Arg Glu Lys Leu Ala Glu
225                 230                 235                 240
Ser Leu Arg His Glu Asn Leu Gln Lys Arg Glu Ser Ile Ser Glu Leu
                 245                 250                 255
Ile Ser Leu Arg Met Phe Leu Asn Asp Thr Leu Ser Thr Phe Asp Asp
             260                 265                 270
Leu Glu Lys Ala Lys Thr His Leu Val Val Leu Trp Ala Ser Gln Ala
         275                 280                 285
Asn Thr Ile Pro Ala Thr Phe Trp Ser Leu Phe Gln Met Ile Arg Asn
    290                 295                 300
Pro Glu Ala Met Lys Ala Ala Thr Glu Glu Val Lys Arg Thr Leu Glu
305                 310                 315                 320
Asn Ala Gly Gln Lys Val Ser Leu Glu Gly Asn Pro Ile Cys Leu Ser
                 325                 330                 335
Gln Ala Glu Leu Asn Asp Leu Pro Val Leu Asp Ser Ile Ile Lys Glu
             340                 345                 350
Ser Leu Arg Leu Ser Ser Ala Ser Leu Asn Ile Arg Thr Ala Lys Glu
         355                 360                 365
Asp Phe Thr Leu His Leu Glu Asp Gly Ser Tyr Asn Ile Arg Lys Asp
    370                 375                 380
Asp Ile Ile Ala Leu Tyr Pro Gln Leu Met His Leu Asp Pro Glu Ile
385                 390                 395                 400
Tyr Pro Asp Pro Leu Thr Phe Lys Tyr Asp Arg Tyr Leu Asp Glu Asn
                 405                 410                 415
Gly Lys Thr Lys Thr Thr Phe Tyr Cys Asn Gly Leu Lys Leu Lys Tyr
             420                 425                 430
Tyr Tyr Met Pro Phe Gly Ser Gly Ala Thr Ile Cys Pro Gly Arg Leu
         435                 440                 445
Phe Ala Ile His Glu Ile Lys Gln Phe Leu Ile Leu Met Leu Ser Tyr
    450                 455                 460
```

|  |  |  |  |  |  |  |  |  |  |  |  |  |  |
|---|---|---|---|---|---|---|---|---|---|---|---|---|---|
| Phe | Glu | Leu | Glu | Leu | Ile | Glu | Gly | Gln | Ala | Lys | Cys | Pro | Pro | Leu | Asp |
| 465 |  |  |  | 470 |  |  |  |  | 475 |  |  |  |  | 480 |

Gln Ser Arg Ala Gly Leu Gly Ile Leu Pro Pro Leu Asn Asp Ile Glu
                485             490             495

Phe Lys Tyr Lys Phe Lys His Leu
            500

(2) INFORMATION FOR SEQ ID NO:9:

(i) SEQUENCE CHARACTERISTICS:
       (A) LENGTH: 5537 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:9:

```
TTTTTGGTTA TCTTTTCAGC CGTGCCCCAC TCTACTGGTA CCAGTTTACT GTATTAGTCG        60
ATTTTCATGC TGCTGATAAA GACATACCTG AAACTGGACA ATTTACAAAA GAAAGAGGTT       120
TATTGGACTT ACAATTCTAC ATCACTTGGG AGGCCTCACA ATCATGATGG AAGGAGAAAG       180
GCACATCTCA CATGGCAGCA GACAAGAAAA GAGCTTGTGC AGGGAAACTC CTCTTTTTAA       240
AACCATCAGA TCTCATGAAA TTATTCATT ATCATGACAA TAGCACAGGA AGAACTGCA         300
CCCATAATTC AGTCACCTCC TACCAGGTTC CTCCCACAAC ACGTGAGAAT TCAAGATGAG       360
ATTTGGATGG GGACACAGCC AAACCATGTC ACACTACCAT GCCTGACTTC CTTTCCATTT       420
TTGTATATTT GCTTGTTCTT CATTTGCCCG AGAAGTAACT CTAAAGGGCT GTATTATTTG       480
GATATTAGAT TGGCATTTTA TCTGACTGGG ATATCTTGCT GTGATTGTCC ATGTATAAGA       540
TCAGCTTTTC TATAAGCCAT ATTTTAAAA AGATATATTA ATTTTTAAA AATCCACCTG         600
TCTAAATAAA TGCACAAAGC CCCCAAAAA CCTAGATTCT AAGAAAATC TATGTACTGC         660
CATACAATGA TTGATATTAA TATTTATGGT GATAAATTAC ACACAAAAA TGTGTGATCT       720
CTGTTTAAAC AGGCAAAAAC AAAAAACACA TGAAATAAAT CTATGGCATC TATAGCCAAA       780
ACTGGAAACA ACCCACATAT CCATCAATAG GAAATCAGTT AAATAAATTA TAGTACATTT       840
ATCCAATGGA AGATTAAGCA CATATTCAAT ATAATTATTT ATACACACAT ATAGATACAC       900
ACATGTATAA ATATAGAGAA TACTGTGGGT GTATGTGTGT GTGTTTAT ATACATATAT        960
ATACACACAC AGTACTGTTG CCTACCTTCT TTTGTCTTAA TTCTGTGAAC TCTCATTCAC      1020
TCTGCTTCAG TAGGATACCT CCTTCTTTTT GGTTCTTAGA CTCACCAAGT TGATCCTTGA      1080
CTCAAGACAT TGCATTTGCT GCTTCCTCTT CCTGGAATAT CCTTCCTTCT GATATTCACA      1140
TGAGTAGTCT CTTCTTGTCA TTCAGATCTC AAATGTCACA ATTCAGAGA GCCCATCTCT       1200
GATCATCATA TCTAAAGTTG TCCTCATTCC CCCATAGCTT TCTATACCAT GTTTATTTT       1260
TTTCATAACA TGTATTTTAT TACTCCTTTC TCCATTGGAA TAGAATCTCC ATTAGATTAG      1320
GAAATCTGCC TATCTTATTA ATGCCTGCAA CTGGAATACT TTGAAGAGT TCTTGGCACG       1380
TAATAAATAC TCAACTAATA TTTTGTGTA CACAGAAATA AAGTTTGGAA GAACAGATGC      1440
CAAATTGTTA CTAGTGGTTA CTTCTGAGTA AAGGAGTAGC ATGGTAGGTA AATTATTAAT      1500
AGATGTTCAC TTTCCACCAA GATATGTTTT AGTTAGTCTT AACTTACTTG AAATGAAATT      1560
TATTACTTTA ATAATTAGAA ACATTGATAA ACATTTTAGT CACAAGAATG ATAGATAAAA      1620
TTTTGATGCT TCCAATAAGT TATATTTATC TAGAGGATGC ACTTATGTAG AATACTCTCT      1680
TGAGGATGTT AGGTGAGTAA CATGTTACTA TATGTAGTAA AATATCTATG ATTTTATAAA      1740
```

```
AGCACTGAAA CATGAAGCAG CAGAAATGTT TTTCCCAGTT CTCTTTCCTC TGAACTTGAT    1800
CACCGTCTCT CTGGCAAAGC ACCTAAATTA ATTCTTCTTT AAAAGTTAAC AAGACCAAAT    1860
TATAAGCTTG ATGAATAACT CATTCTTATC TTTCTTTAAA TGATTATAGT TTATGTATTT    1920
ATTAGCTATG CCCATCTTAA ACAGGTTTAT TTGTTCTTTT TACACATACC AAACTCTTAA    1980
TATTAGCTGT TGTCCCCAGG TCCGAATGTT AAGTCAACAT ATATTTGAGA GACCTTCAAC    2040
TTATCAAGTA TTGCAGGTCT CTGATTGCTT TGGAACCACT TCTGATACCT GTGGACTTAG    2100
TTCAAGGCCA GTTACTACCA CTTTTTTTTT TCTAATAGAA TGAACAAATG GCTAATTGTT    2160
TGCTTTGTCA ACCAAGCTCA AGTAATGGA TCTGGATACT ATGTATATAA AAAGCCTAGC     2220
TTGAGTCTCT TTTCAGTGGC ATCCTTCCCT TTCTAATCAG AGATTTTCTT CCTCAGAGAT    2280
TTTGGCCTAG ATTTGCAAAA TGATGACCAC ATCTTTGATT TGGGGGATTG CTATAGCAGC    2340
ATGCTGTTGT CTATGGCTTA TTCTTGGAAT TAGGAGAAGG TAAGTAATGT TTTATCTTTA    2400
AATTGCTCTT TGATTCATCC ATTTAATTTT TTTACCTTCA TTTTTATACA GTAAATTTGG    2460
TTTTCTATAC TTACACATAT TAGCATTATC TTCCTTATGT TTTAAATGAA AAATTTGATT    2520
TGAATTTTTA AAGTAATATC TTTTTTACTA TATCTCACAA GACATATGAC AGCTTCCCTT    2580
TTTAGTATTG GCATATACCG ATGGTAATAT ATAAATGTAT ATTGGTGTTA AACATAACTG    2640
ACAGAAATTG TATAAGGTCT CTATGTACAT TTATATGTGT ATCTAAAGAG GAAGCCCAGA    2700
TTAGTAAGGA TACAAGTAGC AAGTGGGAAT CTACAATGGA AAGGATTGCT TTCTCTCACA    2760
TGGCTTCAAT AGATACTCTT GCTTAAATAA ATGTTCTCTT TTAAGCTCAT TCTTGTGCAT    2820
CGCATAGACT CAGCCTAAGC CTGAACAAGA GCATAGAGCC TGAGCTGATC ATTCTATTAC    2880
TGTTTTTAAA TAAATGTTAA TCAACTGTGG TGAATTGGGA AAGTTTGCTG AGTGTATGTG    2940
ACATCGATTT CATTTATTTA CAACTGGTTC AAGAATGCAA GAAAACAAA TACAGTCAGA     3000
TCCAGAACCA TAGTTTATTT AACTTCTAAT TGGCTCAAGG AGTAATTGTG GGGAGGCATA    3060
TAGATATTCT CTGCTATGTC AATCTCAAAA AGAGAAAATA ACCCTAACCA TCTTTCAGCT    3120
TTGTAGATTG CTATGTGTTT TCTGCCTTTG CAGTTTCTTT CAGGCCTGAT AGTTTTACT     3180
TTTAATTAAA CTACTTATCT TCAAACTAAG AAAAGAAAGG TAATTACTTT ATACTGTATT    3240
ATTCTATCAA GAGGTACAGA AGTTTATGTT GGAAAATAAG TTTACATGTT CTAATAAAAA    3300
CATTTTAAAG GAGCACTGAA TTACAATAGA TGATTCCGTC AGTGTTTATC TTACTCAATT    3360
TCATTTATA ATAAGCTGAT TTCTCACATG AGATTCTTCT TCTCTGAAAC CATCCTTATA     3420
GAATATAATA TAGATATCTT TAAACTAGGA ATATTTCAA AACCTCAGTT CTGAAATCCT     3480
CCCTTATTCA GTGATCTGTG TCTTTAAAGA AAATAATCAA AAGAAACATT TTGAGATATT    3540
TAGAAAAATG ATGCTTAGCA AAGTGATAAA CACTAGAATG TAGTTTTGTT TCCGCACTGA    3600
CAACAAGAAT CTTGTTGGTC TTGTAAATCC TTTGCCTGT ATCACTGGGA AAAGTGATGA     3660
GCACATAGTA GACGGGTGCT TGTTGAATGT GTATATGGAC GGATGCATGA ATGGATGGAT    3720
TTAGTAATCC TTTCCACCAA CATATCATGT TACTAGGTTA ATATAACCTA TTACTGTAGT    3780
AAAAGAGCAG GGCCCATCCA ACAAAGAAA TATCTATAAA CTATAGGGTT TCAAAGTTTG     3840
AAGTCAGTGG GAAAAATTTT AAAACCTGAT GTAAGTAAAA ACCCAAAACT GTAATCATCC    3900
ATGTCTATCA TACACTTGTG TCTGACAGGC AAACGGGTGA ACCACCTCTA GAGAATGGAT    3960
TAATTCCATA CCTGGGCTGT GCTCTGCAAT TTGGTGCCAA TCCTCTTGAG TTCCTCAGAG    4020
CAAATCAAAG GAAACATGGT CATGTTTTTA CCTGCAAACT AATGGGAAAA TATGTCCATT    4080
TCATCACAAA TCCCTTGTCA TACCATAAGG TGTTGTGCCA CGGAAAATAT TTTGATTGGA    4140
```

-continued

| | | | | | | |
|---|---|---|---|---|---|---|
| AAAAATTTCA | CTTTGCTACT | TCTGCGAAGG | TAAGCAGTTT | TACATTTATA | TACCATTCTG | 4200 |
| TTTGTCTTCT | ACCTTTTTAT | GTGCTTGTCT | ATTTAGAAAT | TTTGATGTAC | TTAGATTTTA | 4260 |
| TGATAAAGGT | GTTGAAGAGA | GTTATCCTTA | TGTGGAGATT | CTTAGAAACA | TAAATAAATT | 4320 |
| ATACGTAGCT | TCTTAGTAAT | AATCATTTAG | AAAGTCAAAA | TAGGTATAGA | TTTCCGTCAT | 4380 |
| TTGCTTTGCA | CGAGCTAATG | AGGGTGAAAT | ACAGATTAAA | TGCTCTACTG | AGACAGGTGG | 4440 |
| CACTGTACGA | ATAAGATAGA | TTAAAATTCA | TCACATCAGC | AATGTCTATG | CAGAGCGAAG | 4500 |
| TGACGGAAAC | CTAACATTCA | GCAGTTGTCT | CACCACACTT | GTGCCACACA | GTGTTTCATT | 4560 |
| TTGATAAGGA | ATTGGCAAGA | TATTTTAACA | TCATTTAGAT | GTAATAAAAG | AAGATCTGTT | 4620 |
| ACTGAGAAAA | AAAACCAATA | ACTACTTACT | TACTGCAAAT | AAATATTAGC | TTTGGTCTTT | 4680 |
| GTGACTAAGT | AGCTTAAAGT | TTGGTTAAAA | TACATCTACA | GCTGGACACA | ATGGAACACA | 4740 |
| CCTGTAGTCC | CTGCTATTTG | AGAGGCTGAG | GCAGGAGGAT | CGCTTGAGTC | CAGGAGTTTG | 4800 |
| AGGCTGCAGT | GAGCTATCAT | TGTGTCACTG | CACTCCAGCC | TGGGTGACAA | TGTGAGACCC | 4860 |
| CATCTCTAAA | AGAAAAAGAA | AAAGAAATCT | ACAAATAATA | TAAAAGATAA | CTAATGATTT | 4920 |
| TAAAACATTA | TCAATTAGTT | TATGTGCAAT | AGCTGTAAAT | AAGTGCAGTA | GCATAAGAAA | 4980 |
| TAAGACATAG | ATGACTTGAG | TGATCCAGGG | GAGTGCCACT | GAAGTTGGCT | TTAAAGGAAA | 5040 |
| GGTACAGTTT | GGTCATTTAT | TTGTAAAGTG | CTATGAACTT | GTACAAGGGA | AAGCCAATTT | 5100 |
| CCCGTGTTTA | CCAAGTAAGG | AACTATGAAA | GTATCTAATC | CGTTTTCAG | TCATTTACTA | 5160 |
| TGACTAGGTC | AGGTTTAACT | TCTTTTTCTG | CATGTTTTAT | TTGCTATCAG | GCATTTGGGC | 5220 |
| ACAGAAGCAT | TGACCCGATG | GATGGAAATA | CCACTGAAAA | CATAAACGAC | ACTTTCATCA | 5280 |
| AAACCCTGCA | GGGCCATGCC | TTGAATTCCC | TCACGGAAAG | CATGATGGAA | AACCTCCAAC | 5340 |
| GTATCATGAG | ACCTCCAGTC | TCCTCTAACT | CAAAGACCGC | TGCCTGGGTG | ACAGAAGGGA | 5400 |
| TGTATTCTTT | CTGCTACCGA | GTGATGTTTG | AAGCTGGGTA | TTAACTATC | TTTGGCAGAG | 5460 |
| ATCTTACAAG | GCGGGACACA | CAGAAAGCAC | ATATTCTAAA | CAATCTTGAC | AACTTCAAGC | 5520 |
| AATTCGACAA | AGTCTTT | | | | | 5537 |

( 2 ) INFORMATION FOR SEQ ID NO:10:

( i ) SEQUENCE CHARACTERISTICS:
        ( A ) LENGTH: 2575 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| | | | | | | |
|---|---|---|---|---|---|---|
| GAATTCTACT | CTTTAAAGGG | GTGAATATTA | TGGTACTTGA | ATTTATCTC | AAGAAAAATG | 60 |
| AATAAAAAGT | AACTAAATCA | TTGAAAATAT | CTGATGGCAT | GGGGTTTGTG | GGGTAACTGG | 120 |
| CATTCCACAG | TGATTTTCAA | AGGGCTTGTG | CTGTTTTCAT | TTGCTTTGT | TTAGTTATG | 180 |
| GAGCCCTTCC | TTGAAACAAA | CTTCATACTA | CAGTCCTCTT | TCATGAAGCA | GAAGAGGGCA | 240 |
| GTGGGCAGAG | CTCTCCTTTG | GCTTTCTCCC | CCACCACAAC | AGGGAGCCCT | GGAGCTCTAG | 300 |
| GAGAGAAAAT | CTGAAATATA | AAGGGCATGC | ATGTGAGCTG | TGGAGTCCCA | GAGCCCTGGG | 360 |
| TTTGCATCCT | AGATCTGCAA | CTCCCGTGAA | TTGAGTTTTG | GAAGTTGCT | GAAACTCTGA | 420 |
| CCTCCTGTTT | TCTCATGGTA | TTGTTGTAAG | GGTTAAATGA | GACAATGTAT | GTGAAGACCC | 480 |
| TGGCCCCACA | GTAGAGGCTC | TGCACACATT | TCAGCGATAC | TTTCCTCATG | TATTTCCAAA | 540 |

| | | | | | |
|---|---|---|---|---|---|
|AATGTTTTCT|CATTTTCTTA|AAATGTCAGA|AAGAAGACAA|CAGAACTTAC|TTGCCTTTTA 600|
|CAACAGAACA|AATGGAGCAA|GTCAGAGGTC|AAGGTGCTAA|CATTCTTCAT|GGTTCCTCAC 660|
|CACCTTTTGT|TCTGTTAGCC|TATAGGGAAA|AGTCTTCTTT|CTCATCTCAT|TATCTGCAGG 720|
|GGAAAATAGT|ACTTCAGCAA|GTGATCCAGT|TGAAGAACAT|CTCCAGGGCC|ATTAACATAC 780|
|AGAGGTTTGT|TCTACTCTCT|CTGTGCTCCA|TGTCTAAGAA|CCTCAGCCTT|CCTCCTAGGA 840|
|GCTAGGGAAA|GTCAGGAAAG|TGAAAATAGT|ACCCCAGCTA|TGAACTGCC|CTGTGCTGGC 900|
|CTGAGAAGAC|AAGACCAGCT|TCCTCAATGG|CTCAAGATTT|GGTTTCCTTC|AATATGTCCT 960|
|TTTGGAAATA|TGTCCATGAC|ATCGGAGAGA|TAAAGGAGC|CAGGATTGCT|CACATTCAGG 1020|
|AAAAAGCTC|CACTATCTTT|CTCTCTCTCC|CTCTTTCTCT|CCCTCCCCCT|GACTGCCCTC 1080|
|TTCTCTATCT|CTCTCTCTCC|CTGAGCTGGC|AAGGTTAATT|GGTCGCAGAA|AGCCGAAGAA 1140|
|ACAAGTGGGC|CTCCTGGAAC|AAAGTTCAAA|AAGCCGAAAA|CGGGAAGAAA|ACTAACCACA 1200|
|AAAGTAAAGG|AACCACTTAG|CCTTCTTTGA|TTCCAGGCCC|CCAAGCCTGT|CTTTAACTTG 1260|
|GATGAATGGA|GTTCTTCCTG|TGCTACAGCA|CCGCATAGTA|GGGGCTGCCC|TGGGCCTGAA 1320|
|GCCAGAGCTT|CACCATATTC|AGTCATCTGT|ACATTGAGGC|AACAGTGCCT|GCTTCATGGT 1380|
|GCTACCCTGT|GGATTAAATG|AAGCAAGTTT|TTGATGATCT|TGACACTGAA|TATTGATGCA 1440|
|TTGGTCAGAC|TTTTTCTGAT|AGTAAAAAAT|GGTGGTTTCT|TGTTGTCAGA|AATCAAATCA 1500|
|ATATATTTGT|TCTCCTGTTG|ATTAGCTATG|TCCCTAGAG|GGCAGCGACT|TTGCCTGTCT 1560|
|TATTTATCTC|TGCATCTCCA|GCACTTAAAA|GGTGCCTTGC|ATAAGGTACA|TATTAAGTTC 1620|
|ATATGAATGA|ATGAATGAAA|TGCATATGAT|TTATTCATAC|CCAGTTGGTG|GTGTGTTTAC 1680|
|CCTTTCCTAA|ACCTGTAGTC|AGATGGCCTT|TGAATCCCCT|GTACTTCTTG|TGAGGTACTG 1740|
|TGCTGTAAAG|GTGGACTATC|ACACTTCAGT|TCAGAGCAAT|CTGGGCTTGA|ATCCTGGATT 1800|
|TGCCAGTTTA|TTAACTATAG|CAAACATTTT|TGAGCATACA|TTGTGCCAAG|TGCTAGGCTA 1860|
|ACTGTCTTAC|ACACATTGTC|TTATTTCGTC|TTAATATCTA|TGAGTCATGC|ACTATAATCA 1920|
|TCCCCATTTT|ACAGATAAGA|AAGCAAAGAC|TTGGAGAGGA|AAAGCATCTT|GTTCAAAGGT 1980|
|AAATACTTAA|TGGCCAAGCC|AACATGCAAA|TCTAGATTTA|ATTGCAGCTT|CCTCTTCATC 2040|
|TACCATTCGA|ACTAATTCAA|GCTATGTAAT|ATTTCCACT|GAACTTCTT|GCCTCTACTT 2100|
|CCTCATCTTT|AACATGGTCA|AAATACCTGT|CCTGCCCAAG|TTAGTTATTT|CATTAAAGTA 2160|
|GAAAATACA|AGAGAAGCTT|TTAAAATGTG|AAACCTCAAA|TGAATGTAAA|ATTATGATGA 2220|
|TTCCTTTAGA|ATTTGTCAAC|ACCTTCTTTT|CTCTACTCCT|GCTAGGCATT|TACAATCTCA 2280|
|AAACCATGTA|TTTAAGATGC|AAAACTATAT|TTGTATTTGC|CATAACTGGT|TTCTTTCCCT 2340|
|ATGGCTTCAT|GAAAATGTGG|CTCGAATGTG|TTTATTATGA|AAGCCCAAA|TTAATCACGA 2400|
|CAAGACTTCA|CCAGCCCATT|CCACAATAGA|CTCCCATTAC|TTTGCCCTGA|CTTAGAAACC 2460|
|TCATATACAG|TCTTGATTCA|GTACAGCTCT|GTGATGCTCT|TGGAAAATGC|AAAGTGCTTT 2520|
|CTTAATTGAG|GCAATCTGTG|TCCCACTACA|GAGAGGTGGT|TTAACTTGTG|AATTC 2575|

( 2 ) INFORMATION FOR SEQ ID NO:11:

( i ) SEQUENCE CHARACTERISTICS:
        ( A ) LENGTH: 2316 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

-continued

```
AGAGCAACCT GGGCAACATA GCAAAACCCT GTCTCTGCAA ACAATAAAAA GAAGAAAATT      60
AGCTGGGTAT GGTGGCACAT GCTATAGTCG CAGCTACTCG AGAGGTTGAG GTGGGAGGAT     120
CAGTTCAGCC TGGGAGGTTG AGGCTGCAGT GAGCCAGATC ATGCCACTGC ACTGCAGCAT     180
GGGCAACAGA ATGAGACCCT GGCTAAAAGA AAACAAAATA AAAATTCAG ACACAGGTTG      240
AATCATTGAT AACAGCATAG TGGTAACAGA AAGAAAGTTT GGGAAATTTT TATCTGATCA     300
GCTTCCCATA CCCTGTTCAT CTTTGTGTTA TGCACTGCCA GGCTGTCTGT AGGTTCAGAC     360
TCTATATCAT ATGACCTTCA AACACTTGGT TTGTTCTTCT CCTTCCTTCC TCCCTTCTTC     420
TTTCATTTTT TATCTTTTTT TCTTTTAAAA TGTTTAGATA GTATAATAAG GAACTGCTGA     480
GGCTTTCCAG TGCCTCCCTC AACATCCGGA CAGCTAAGGA GGATTTCACT TTGCACCTTG     540
AGGACGGTTC CTACAACATC CGAAAAGATG ACATCATAGC TCTTTACCCA CAGTTAATGC     600
ACTTAGATCC AGAAATCTAC CCAGACCCTT TGGTAAAGTC GCAGTGTGCC CGAATTGAAA     660
TTCAATATCC AGGTGATAGC TACCTAGATC TAAATAAAGA GGAAATTTAC AATGGTAGAA     720
TTGATTTTCT CATAGTAGTC ACAGGAATTG TCTGACTTAA TTGTGTTAAA TATTCATATA     780
TTTTGGAAAA TTAGATAGT GGTCTGAATT TTTCATTTTA GTCCTGATAT TTGCCATCAC      840
ACAGTCTTTG CTAGATTATA TTTGCAGTCA TGATAATAAA CCTGCCACTT TTTTTTTCTT     900
AAAAGCACC TCCTCCCAAA TCCAGGAAAT TGGAGGCTAA TATATTGATT ATTCTAGTTT      960
CTTCTGGGAA CCCTTCTCTC TCTAGCTCTG CCTGACTAAG GAACTAATCG TTCAAGCAGG    1020
ATAGGAAGGT ATCACAAGGC TTCCTTAGCT GCATTAAGCT CCTGTTCCTT ATTACTTTCT    1080
GATTCAATGT GGAGTATTTG CTAAATCACT AATGGGGTAG AATTAAAAAG AAAATTACTC    1140
TTTGGAGCTT CCAGGTTTAG AAAGAGATAA ATTTCTTTAA AACTAGCTTA AAGGCGGTTT    1200
TCTTTGTATT TTTATTGCAG ACTTTTAAAT ATGATAGGTA TCTTGATGAA AACGGGAAGA    1260
CAAAGACTAC CTTCTATTGT AATGGACTCA AGTTAAAGTA TTACTACATG CCCTTTGGAT    1320
CGGGAGCTAC AATATGTCCT GGAAGATTGT TCGCTATCCA CGAAATCAAG CAATTTTTGA    1380
TTCTGATGCT TTCTTATTTT GAATTGGAGC TTATAGAGGG CCAAGCTAAA TGTCCACCTT    1440
TGGACCAGTC CCGGGCAGGC TTGGGCATTT TGCCGCCATT GAATGATATT GAATTTAAAT    1500
ATAAATTCAA GCATTTGTGA ATACATGGCT GGAATAAGAG GACACTAGAT ATTACAGGAC    1560
TGCAGAACAC CCTCACCACA CAGTCCCTTT GGACAAATGC ATTAGTGGT GGCACCACAC     1620
AGTCCCTTTG ACAAATGCA TTAGTGGTG GTAGAAATGA TTCACCAGGT CCAATGTTGT      1680
TCACCAGTGC TTGCTTGTGA AATCTTAACA TTTTGGTGAC AGTTCCAGA TGCTATCACA     1740
GACTCTGCTA GTGAAAAGAA CTAGTTTCTA GGAGCACAAT AATTTGTTTT CATTTGTATA    1800
AGTCCATGAA TGTTCATATA GCCAGGGATT GAAGTTTATT ATTTTCAAAG GAAAACACCT    1860
TTATTTTATT TTTTTCAAA ATGAAGATAC ACATTACAGC CAGGTGTGGT AGCAGGCACC     1920
TGTAGTCTTA GCTACTCGAG AGGCCAAAGA AGGAGGATGC TTGAGCCCAG GAGTTCAAGA    1980
CCAGCCTGGA CAGCTTAGTG AGATCCCGTC TCCAAAGAAA AGATATGTAT TCTAATTGGC    2040
AGATTGTTTT TTCCTAAGGA AACTGCTTTA TTTTATAAA ACTGCCTGAC AATTATGAAA     2100
AAATGTTCAA ATTCACGTTC TAGTGAAACT GCATTATTTG TTGACTAGAT GGTGGGGTTC    2160
TTCGGGTGTG ATCATATATC ATAAAGGATA TTTCAAATGT TATGATTAGT TATGTCTTTT    2220
AATAAAAAGG AAATATTTTT CAACTTCTTC TATATCCAAA ATTCAGGGCT TTAAACATGA    2280
TTATCTTGAT TTCCCAAAAA CACTAAAGGT GGTTTT                              2316
```